United States Patent
Ariav

(10) Patent No.: US 6,984,993 B2
(45) Date of Patent: Jan. 10, 2006

(54) METHOD AND APPARATUS FOR MAKING HIGH-PRECISION MEASUREMENTS

(75) Inventor: Arie Ariav, Doar Na Hof Ashkelon (IL)

(73) Assignee: Nexense Ltd., Yavne (IL)

( * ) Notice: Subject to any disclaimer, the term of this patent is extended or adjusted under 35 U.S.C. 154(b) by 0 days.

(21) Appl. No.: 10/859,154

(22) Filed: Jun. 3, 2004

(65) Prior Publication Data

US 2005/0027206 A1 Feb. 3, 2005

Related U.S. Application Data

(63) Continuation-in-part of application No. 10/844,398, filed on May 13, 2004, which is a continuation-in-part of application No. 10/615,952, filed on Jul. 10, 2003, now Pat. No. 6,856,141, which is a continuation of application No. PCT/IL02/00983, filed on Dec. 5, 2002, which is a continuation of application No. 09/983,430, filed on Oct. 24, 2001, now Pat. No. 6,621,278, which is a continuation-in-part of application No. PCT/IL00/00241, filed on Apr. 27, 2000.

(60) Provisional application No. 60/343,586, filed on Jan. 2, 2002, provisional application No. 60/336,166, filed on Dec. 6, 2001.

(30) Foreign Application Priority Data

Apr. 28, 1999 (IL) .................................. 129651

(51) Int. Cl.
*G01R 27/04* (2006.01)

(52) U.S. Cl. ...................... 324/639; 324/698; 324/204; 324/442; 73/53.05; 600/430

(58) Field of Classification Search .............. 324/639, 324/698, 71.1, 442, 204, 207.17; 340/500, 340/531, 573.1; 600/459, 430, 2; 73/53.05
See application file for complete search history.

(56) References Cited

U.S. PATENT DOCUMENTS

| | | | | |
|---|---|---|---|---|
| 5,841,274 A | * | 11/1998 | Masreliez et al. | ...... 324/207.17 |
| 6,577,112 B2 | * | 6/2003 | Lvovich et al. | ............ 324/71.1 |
| 6,861,851 B2 | * | 3/2005 | Lvovich et al. | ............. 324/698 |

* cited by examiner

*Primary Examiner*—Vincent Q. Nguyen

(57) ABSTRACT

A method and apparatus for measuring a predetermined parameter, by providing a displaceable sensor on a mounting member such that the displaceable sensor changes in location, form or length with respect to the mounting member in accordance with the predetermined parameter. A cyclically-repeating energy wave is transmitted to or through the displaceable sensor, and a predetermined fiducial point in the received cyclically-repeating energy wave is detected and used for continuously changing the frequency of the transmitted cyclically-repeating energy wave such that the number of waves received is a whole integer. The change in frequency is used to produce a measurement of the predetermined parameter. Several embodiments are described wherein the displaceable sensor is a deformable membrane, an end wall of a bellows, a spring-mounted member, a displaceable plunger, and a bar changing its length in accordance with the parameter to be measured.

43 Claims, 15 Drawing Sheets

METHOD AND APPARATUS FOR MAKING HIGH-PRECISION MEASUREMENTS

RELATED APPLICATIONS

The present application is a Continuation of application Ser. No. PCT/IL02/00983, filed Dec. 5, 2002 which claims the priority dates of U.S. Provisional Applications 60/336,166, filed Dec. 6, 2001, and 60/343,586, filed Jan. 2, 2002. The present application is also a Continuation-in-Part of U.S. patent application Ser. No. 10/844,398, filed May 13, 2004, which in turn is a Continuation-in-Part of U.S. patent application Ser. No. 10/615,952 filed Jul. 10, 2003 now U.S. Pat. No. 6,856,141, which in turn is a Continuation of U.S. patent application Ser. No. 09/983,430 filed Oct. 24, 2001, now U.S. Pat. No. 6,621,278, issued Sep. 16, 2003, which in turn is a Continuation-in-Part of application Ser. No. PCT/IL00/00241 filed Apr. 27, 2000 which claims the priority date of Israel Application 129,651, filed Apr. 28, 1999.

FIELD AND BACKGROUND OF THE INVENTION

The present invention relates to a method and apparatus for measuring, with extremely high precision, a predetermined parameter, such as displacements (e.g., physical movements or deformations) of or in a body, temperature of a body, strain in a body, and many other characteristics or conditions influencing, in a known or predeterminable manner, the transit time of energy (electromagnetic or sonic) from an energy transmitter to a receiver.

As briefly described in the above-cited International Applications, systems involving the detection and/or measurement of body displacements are used in a wide variety of medical fields. One important use is as an apnea detector for detecting cessation of breathing particularly of infants, to prevent SIDS (Sudden Infant Death Syndrome), as described for example in U.S. Pat. No. 6,150,941. Another use is for preventing bedsores (decubitus ulcers). Further applications are for monitoring irregular breathing while sleeping, or for monitoring various cardiovascular conditions such as pulse rate, blood pressure, cardiac output and the like. For example, U.S. Pat. No. 5,853,005 illustrates an acoustic monitoring system for monitoring many different type of body functions based on the use of a sensor pad for sensing acoustic signals originating from the body being monitored.

The above-cited International Application PCT/IL00/00241 describes a method, and also apparatus and a probe for use in such method, of measuring a predetermined parameter having a known relation to the transit time of movement of an energy wave through a medium, by: transmitting through the medium a cyclically-repeating energy wave; receiving the cyclically-repeating energy wave transmitted through the medium; detecting a predetermined fiducial point in the received cyclically-repeating energy wave; continuously changing the frequency of transmission of the cyclically-repeating energy wave in accordance with the detected fiducial point of each received cyclically-repeating energy wave such that the number of waves received is a whole integer; and utilizing the change in frequency to produce a measurement of the predetermined parameter. That application describes many uses of such a method, as well as of apparatus and a probe for implementing the method, in many fields, both medical and non-medical, for providing measurements having a much higher degree of precision than otherwise practically attainable.

The above-cited International Application PCT/IL02/00854 describes such a method in which the transmitted and received cyclically-repeating energy wave is an electromagnetic carrier wave amplitude-modulated by a cyclically-repeating modulating wave; the received amplitude-modulated carrier wave being demodulated, and the fiducial point of the demodulated wave being utilized to change the frequency of the modulating wave such that the number of received demodulated waves is a whole integer. Such a method enables the use of high frequency, compact, narrow-beamed antennas or optical systems for transmission and reception.

International Application PCT/IL02/00854 also describes a method and apparatus of making measurements according to the above-cited PCT/IL00/00241 wherein the phase of the received cyclically-repeating energy wave is shifted by a whole-integer multiple of 360° before being utilized to change the frequency the energy wave is transmitted through the medium. This feature adds an artificial distance to the measurement, e.g., when a relatively high frequency is used and therefore a relatively small wavelength is involved, or when otherwise there is a relatively short transit distance between the transmitter and the receiver.

OBJECTS AND BRIEF SUMMARY OF THE PRESENT INVENTION

An object of the present invention is to provide further methods and apparatus, particularly based on the method of one or both of the above-cited PCT Applications, for making other types of measurements requiring high precision and/or sensitivity.

According to one aspect of the present invention, there is provided a method of measuring a predetermined parameter, comprising: mounting a displaceable sensor on a mounting member such that the displaceable sensor changes its location, form or length with respect to the mounting member in accordance with the predetermined parameter; transmitting a cyclically-repeating energy wave through a transmission channel to or in the displaceable sensor; receiving the cyclically-repeating energy wave transmitted through the transmission channel to or in the displaceable sensor; continuously changing the frequency of transmission of the cyclically-repeating energy wave in accordance with changes in the predetermined parameter such that the number of waves received is a whole integer; and utilizing the change in frequency to produce a measurement of the predetermined parameter.

A number of embodiments of the invention are described below for purposes of example. According to various described embodiments, the displaceable sensor may be a deformable membrane, and end wall of a bellows, a spring-mounted member, or a bar or strip whose length and/or form changes in accordance with the predetermined parameter.

According to some described preferred embodiments, the displaceable sensor is constructed so as to be exposed for direct contact with a body such that the location or form of the sensor is changed by the body in accordance with the parameter to be measured, thereby changing the transit time of the cyclically-repeating energy waves transmitted to and reflected from the displaceable sensor in accordance with the parameter to be measured.

In other described preferred embodiments, the displaceable sensor is constructed so as to be changed in location or form by a part of a person's body which pulsates according to the breathing rate and/or pulse rate of the person, the breathing rate and/or pulse rate being the parameter to be measured.

Further embodiments are described wherein the displaceable sensor is constructed for direct contact with a body so as to be changed in length in accordance with the parameter to be measured, thereby changing the transit time of the cyclically-repeating energy waves transmitted through the displaceable sensor in accordance with the parameter to be measured. Examples of the latter embodiments include implementations of the invention as a thermometer for measuring temperature, or as a strain gauge for measuring mechanical forces.

According to another aspect of the invention, there is provided apparatus for measuring a predetermined parameter, comprising: a displaceable sensor carried by a mounting member such that the displaceable sensor changes in location, form or length with respect to the mounting member in accordance with the predetermined parameter; a transmitter for transmitting a cyclically-repeating energy wave through a transmission channel to or in the displaceable sensor; a receiver for receiving the cyclically-repeating energy wave transmitted through the transmission channel to or in the displaceable sensor; and a data processor for continuously changing the frequency of transmission of the cyclically-repeating energy wave in accordance with changes in the predetermined parameter such that the number of waves received is a whole integer and for utilizing the change in frequency to produce a measurement of the predetermined parameter.

Because of the high accuracy and/or sensitivity attainable by apparatus constructed in accordance with the foregoing features such apparatus may be used in a large number of medical and non-medical applications. Among the medical applications described below are in a mattress or seat to be occupied by a person in order to measure the respiratory rate or pulse rate of the person. Such apparatus may also be incorporated in a harness for application to the body of a person for measuring the person's respiratory conditions, in a cuff for application to a limb of a person for measuring a cardiovascular condition of the person, or in a finger probe to be engaged by the person for measuring a cardiovascular condition of the person. Other possible medical applications include as a probe for sensing pulsatile blood flow (e.g., to identify an artery), or for distinguishing cancerous tissue from non-cancerous tissue, in a real-time manner, e.g., during a surgical operation.

Possible non-medical applications described below include; measuring the temperature within a heated chamber, measuring strain or weight, producing high-precision measurements regarding occupants of a motor vehicle, detecting intrusions by unauthorized persons into a motor vehicle or other secured areas, and monitoring the composition of lubricating oil in a motor vehicle to provide an indication when the oil, and/or the oil filter, should be changed.

Further features, advantages and applications of the invention will be apparent from the description below.

BRIEF DESCRIPTION OF THE DRAWINGS

The invention is herein described, by way of example only, with reference to the accompanying drawings, wherein:

FIG. 11 illustrates the invention implemented in a finger probe, e.g., for measuring a person's pulse rate, respiration rate, or the like;

DESCRIPTION OF PREFERRED EMBODIMENTS

Figure 1:
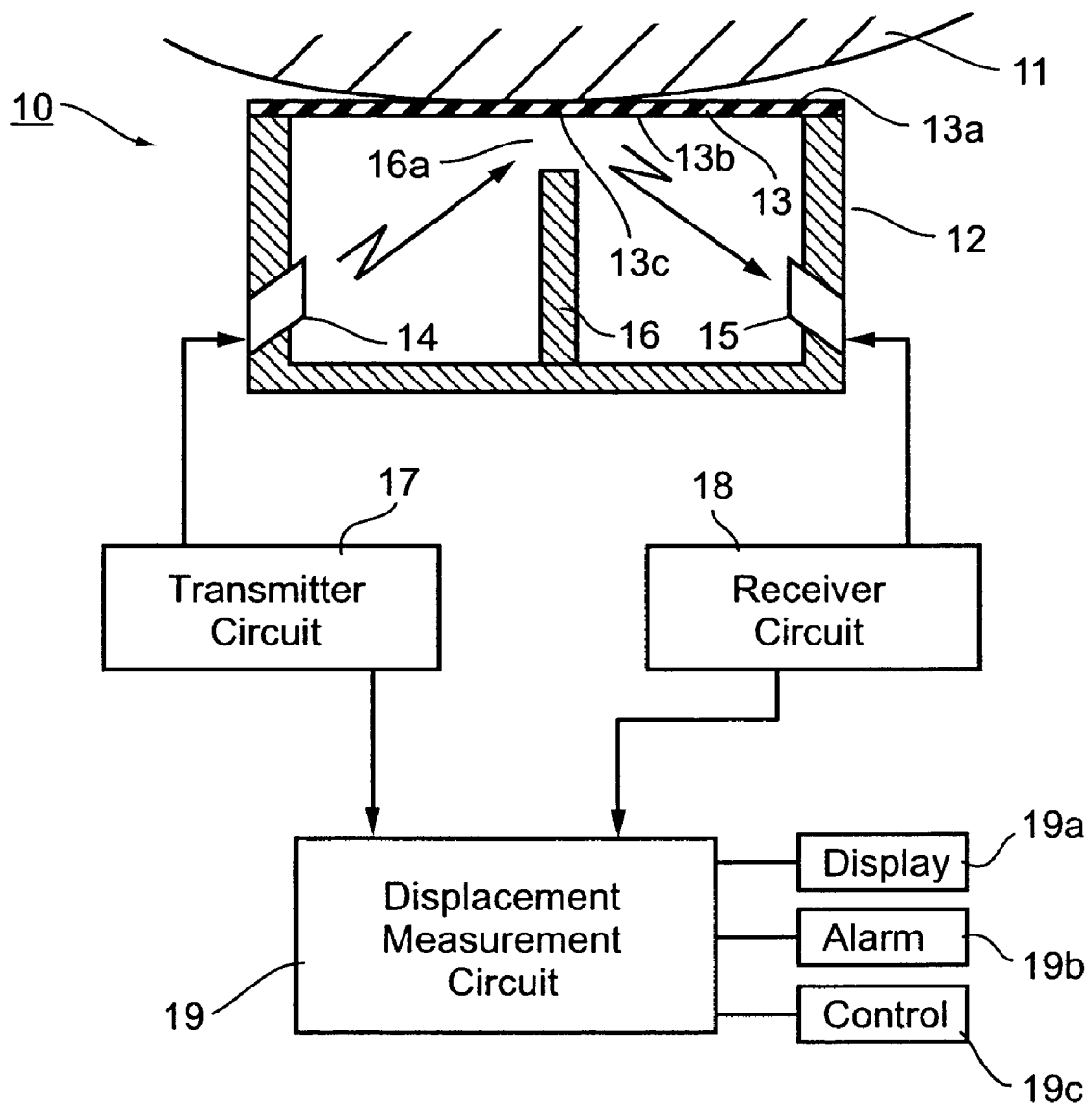
FIG. 1 is a diagram illustrating one form of apparatus constructed in accordance with the present invention for measuring displacements of a body, the apparatus in FIG. 1 including a membrane-type probe for detecting the displacements to be measured.

The apparatus illustrated in FIG. 1 includes a probe, generally designated 10, for detecting and measuring the displacements of a body 11. For this purpose, the probe 10 includes a housing 12 closed at one side by a displaceable sensor in the form of a deformable membrane 13, preferably a thin membrane of elastomeric material. The outer face 13a of membrane 13 is to be brought into direct contact with the body 11 or a part thereof such that the membrane is displaced (in this case, deformed) by the body or part thereof contacted by the membrane.

Housing 12 further includes, on one side of its interior, a transmitter 14 for transmitting a succession of energy pulses towards the inner face 13b of membrane 13, and on the opposite side, a receiver 15 for receiving the echoes of the energy pulses after reflection from the inner face 13b of membrane 13. Receiver 15 is preferably separated from transmitter 14 by a separator wall 16. Wall 16 is spaced from the inner face 13b of membrane 13 to define a gap 16a underlying the center region 13c of membrane 13 such that the echoes received by the receiver 15 are those reflected from the central region 13c.

The apparatus illustrated in FIG. 1 further includes a transmitter circuit 17 for driving the transmitter 14 to transmit a succession of energy pulses towards the inner face 13b of membrane 13, and a receiver circuit 18 connected to the receiver 15 which receives the echoes of the energy pulses after reflection from the inner face 13b of membrane 13.

The illustrated apparatus further includes a displacement measurement circuit 19. This circuit measures the transit times between the instant of transmission of an energy pulse and the reception of its echo, and utilizes the measured transit times to produce a measurement of the displacement of membrane 13, and thereby of body 11.

Figure 6:
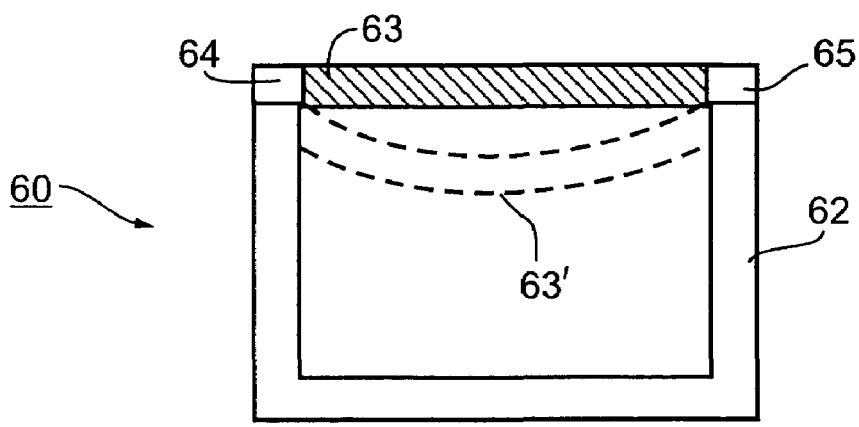
FIG. 6 is a diagram illustrating another type of probe constructed in accordance with the invention for measuring or detecting changes in length in the displaceable sensor.

Many echo systems are known for measuring the distance of a target, in this case membrane 13, by measuring the transit time taken by a transmitted energy pulse until its echo is received. FIG. 6, to be described below, illustrates a preferred system constructed in accordance with my above-cited International Applications. Such a system enables measurements to be made with an extremely high degree of accuracy, in the order of microns and even fractions of a micron, even with relatively large working distances between the transmitter 14 and the receiver 15.

The output of measurement circuit 19 may be connected to a display 19a for displaying in real-time the displacement measurements, and/or to an alarm 19b to be actuated when a displacement of a predetermined value is or is not detected, (e.g., for a predetermined time interval, to indicate an apnea episode, or a danger of developing a bedsore). The output of circuit 19 may be also connected to a control system 19c, e.g., to control the position of a mattress or the pressure of a variable-pressure airbed supporting a patient in order to prevent the development of a bedsore, to control a recorder for recording the detected displacements, etc.

Figure 2:
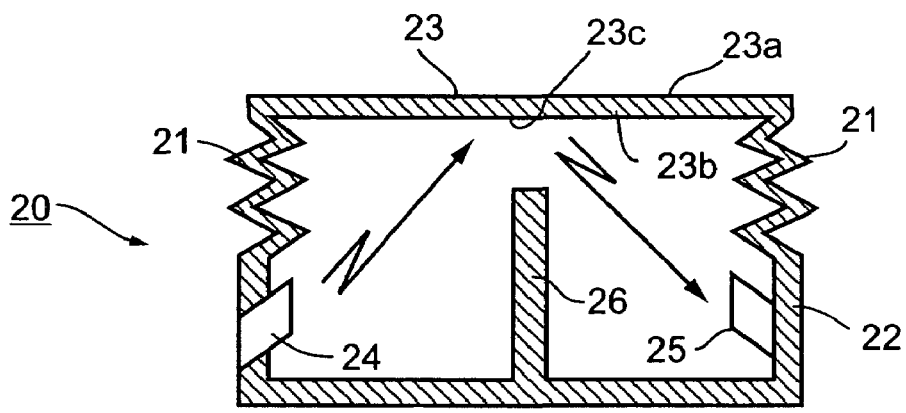
FIG. 2 is a diagram illustrating a bellows-type probe constructed in accordance with the present invention.

FIG. 2 illustrates another probe, generally designated 20, also including a housing 22 mounting a displaceable sensor 23 to be brought into contact with the body such that the displaceable sensor changes its location by the body. In this case, the displaceable sensor 23 is an end wall of a bellows 21 integrally joined to the housing 22 such that the outer face 23a of the end wall is exposed for contact with the body (11 FIG. 1), whereas the inner face 23b of the end wall faces inwardly of the housing 22.

As in FIG. 1, housing 22 further includes a transmitter 24 at one side, and a receiver 25 at the opposite side separated from the transmitter by a separator wall 26. Separator wall 26 is spaced from the inner face 23b of the displaceable end wall 23 to allow the receiver 25 to receive the echoes of the energy pulses transmitted by the transmitter 24 after reflection from the center region 23c of the displaceable end wall 23.

In all other respects, the probe 20 illustrated in FIG. 2 is constructed and operates in the same manner as described above with respect to probe 10 illustrated in FIG. 1.

Figure 3:
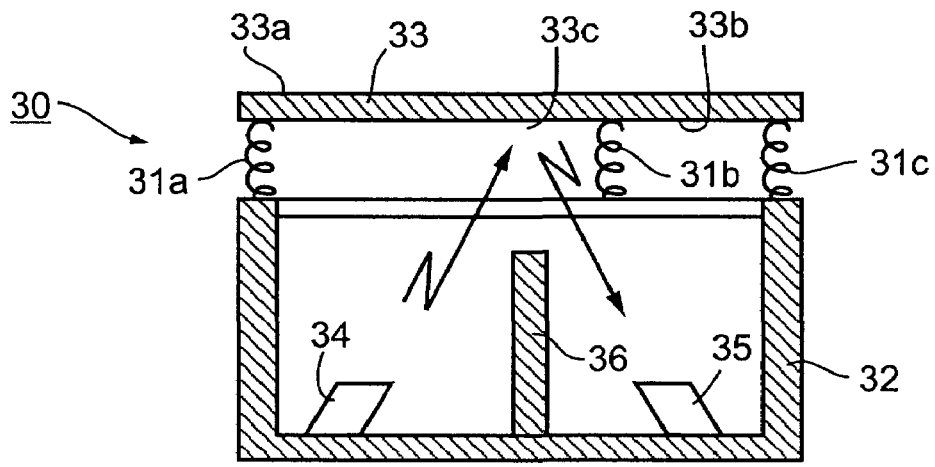
FIG. 3 is a diagram illustrating a spring-type probe constructed in accordance with the invention, FIG. 3a being a top plan view of the probe of FIG. 3.
Figure 3A:
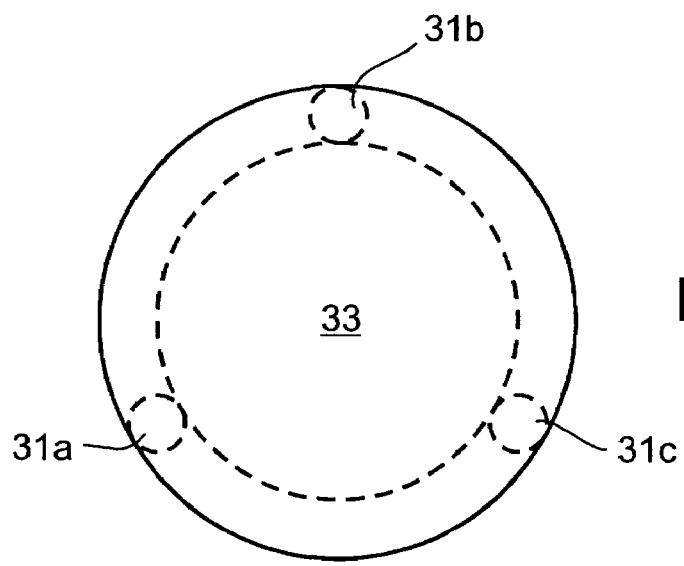

FIGS. 3 and 3a illustrate another probe, generally designated 30, also including a housing 32 carrying a displaceable sensor 33 adapted to be brought into contact with the body whose displacements are to be detected and/or measured. In this case, the displaceable sensor 33 is a movable plate which is spring-mounted by a plurality of coil springs 31a, 31b, 31c to the housing 32. FIG. 3 illustrates the plate 33 as being of circular configuration and supported by three coil springs, but it will be appreciated that the plate could be of rectangular or other configuration, and could be supported by a different number of springs.

Probe 30 illustrated in FIGS. 3 and 3a also includes a transmitter 34 at one side of the housing, and a receiver 35 at the opposite side of the housing separated from transmitter 34 by a separator wall 36 such that the receiver receives the echoes of the transmissions from transmitter 34 after reflection from the central region 33c of the inner face 33b of plate 33.

Figure 4:
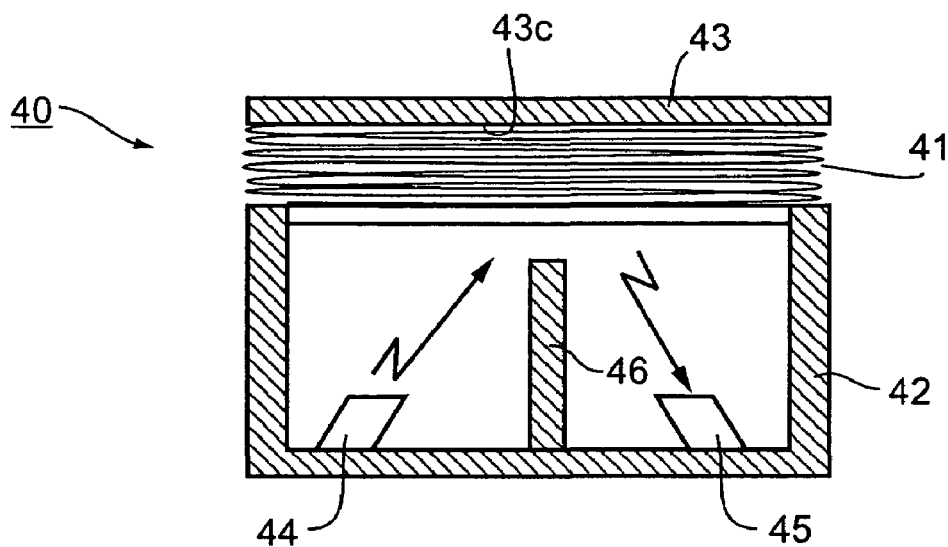
FIG. 4 is a diagram illustrating another spring-type probe constructed in accordance with the present invention.

FIG. 4 illustrates another probe, generally designated 40, also of the spring type, including a housing 42 mounting a displaceable sensor in the form of a movable plate 43 such as to enable the outer face 43a of plate to be brought into contact with the body whose displacements are being measured. In this case, displaceable plate 43 is mounted to housing 42 by a single coil spring 41 coaxial with housing 42 and engageable with the circumference of the housing and the displaceable plate 43.

Probe 40 illustrated in FIG. 4 also includes a spring 41 mounting a displaceable plate 43 to a housing 42 containing a transmitter 44 in one side and a receiver 45 in the opposite side. A separator wall 46 separates the transmitter from the receiver but permits the energy pulses transmitted by the transmitter to be received as echoes after reflection from the central region 43c of the inner face of the displaceable plate 43.

Figure 5:
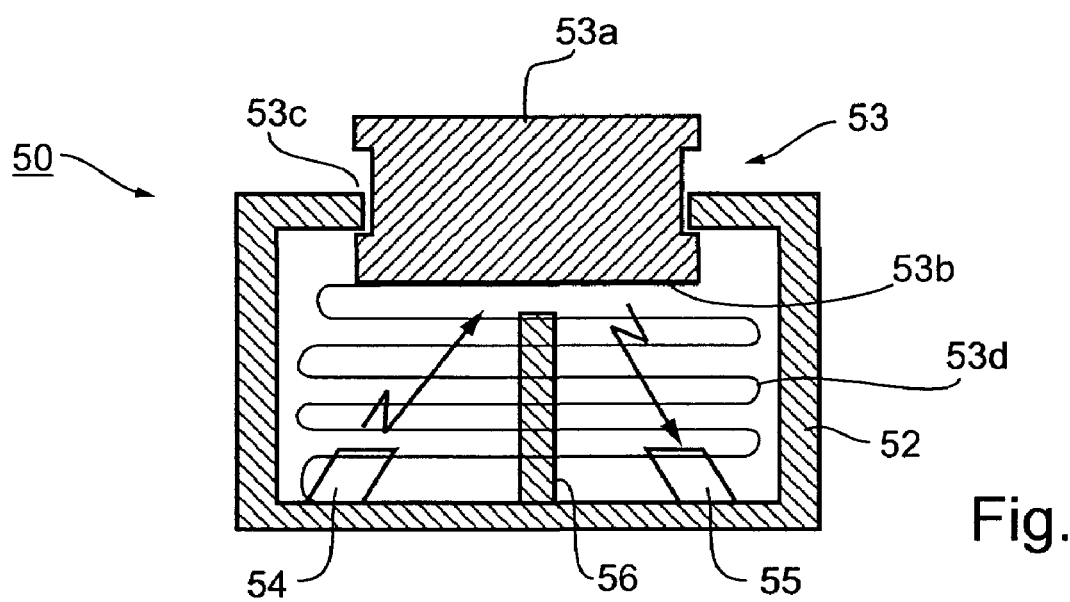
FIG. 5 is a diagram illustrating a plunger-type probe constructed in accordance with the present invention.

FIG. 5 illustrates a plunger-type probe, generally designated 50, including a housing 52 mounting a plunger-type displaceable sensor 53. Displaceable plunger 53 includes an outer face 53a, an inner face 53b and a connecting stem 53c. The outer face 53a of the displaceable plunger is to be brought into contact with the body whose displacements are to be detected and measured; whereas the inner face 53b faces a transmitter 54 and a receiver 55 within the housing 52 and are preferably separated by a separator wall 56 such that the energy pulses transmitted by transmitter 54 are reflected from face 53b to the receiver 55. Plunger 53 is urged outwardly of housing 52 by a coil spring 53d to cause the plunger to be displaced by and with the body (11, FIG. 1) whose displacements are to be detected and measured.

In all other respects, probes 30, 40 and 50 illustrated in FIGS. 3, 4 and 5 constructed and operate in the same manner as described above with respect to FIG. 1.

While in the probes of FIGS. 2–5 described above the displacement detected or measured is a physical movement or change in location of a displaceable sensor, FIG. 6 illustrates a probe wherein the displacement detected or measured is a change in length of the displaceable sensor.

Thus, the probe illustrated in FIG. 6, and therein generally designated 60, includes a housing 62 closed at one end by a deformable member, such as a membrane 63. The housing, or membrane, carries a transmitter 64 at one end, and a receiver 65 at the opposite end. Thus, the deformation of membrane 63, as shown by broken line 63', will increase its length, and thereby the transit distance between the transmitter 64 and receiver 65, so that an accurate measurement of the transit time of a sonic pulse transmitted by transmitter 64 and received by receiver 65 will provide a measurement of the degree of deformation of the membrane 63. Probe 60 is in FIG. 6 would also include a transmitter circuit 17, receiver circuit 18, and displacement measurement circuit 19, for measuring the transit time of pulses from the transmitter to the receiver, and thereby the degree of deformation of the displaceable sensor 63.

As indicated earlier, the circuitry included within blocks 17, 18 and 19 of probe 10 illustrated in FIG. 1 (and also of the probes illustrated in FIGS. 2–6), is preferably that described in my above-cited International Applications since such circuitry enables the probe to detect and measure displacements with extremely high accuracy, in the order of microns and even fractions of a micron.

Figure 7:
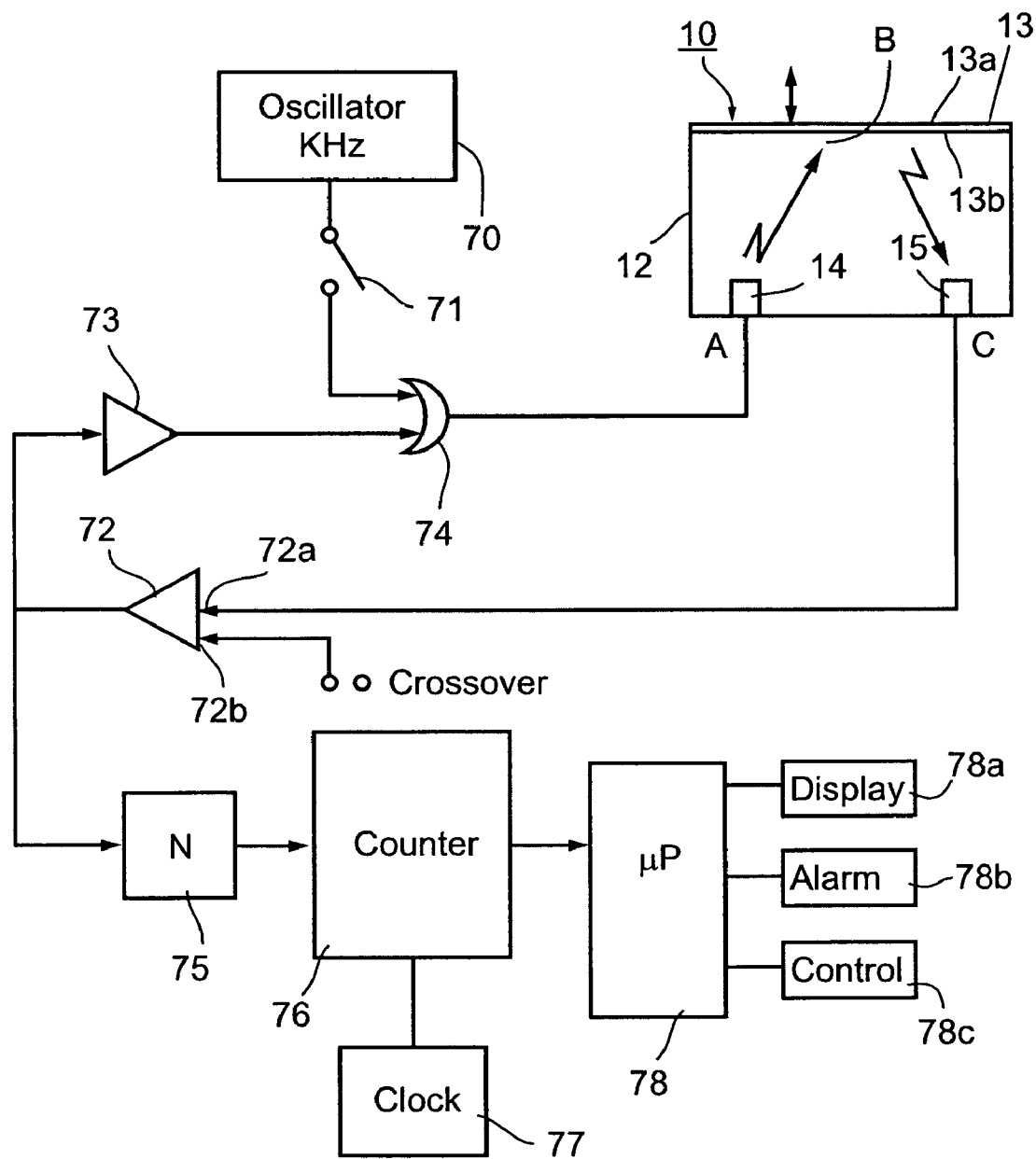
FIG. 7 is a block diagram illustrating a preferred apparatus constructed in accordance with the present invention to include one of the above-described probes and a measuring system as described in my above-cited International Applications.

FIG. 7 illustrates one form of apparatus including a probe constructed in accordance with FIG. 1 having a displacement measuring system 19 of the type described in the above-cited International Applications.

In the probe illustrated in FIGS. 1 and 7, the outer face 13a of displaceable sensor 13 is brought into contact with the body whose displacements are to be detected and measured. A succession of energy pulses, preferably sonic pulses, are transmitted by transmitter 14 located at point A towards point B on the inner face 13b of displaceable sensor 13, while receiver 15, located at point C receives the echoes of the energy pulses after reflection from inner face 13b of displaceable sensor 13. The system illustrated in FIG. 7 measures, with an extremely high degree of accuracy, the transit time between the transmission of the energy pulses from point A, after reflection from point B, until its echo is received at point C. As particularly described in the above-cited International Applications, this is done by: detecting a predetermined fiducial point of each received energy pulse, utilizing the detected fiducial point for triggering the transmission of the next energy pulse in the succession, and measuring the frequency of transmission of the energy pulses in the succession, to produce measurements of the pulse transit times, and thereby of the displacements of the body engaged by the displaceable sensor 13.

More particularly the apparatus illustrated in FIG. 7 operates as follows: Initially, a succession of sonic pulses are continuously transmitted by transmitter 14 as driven by oscillator 70 (switch 71 being closed), until the echoes from the displaceable sensor 13 are received by receiver 15. Once the echoes are received, switch 71 is opened so that the received echo signals are thereafter used for controlling the transmitter 14.

As shown in FIG. 7, the echo signals received by receiver 15 are fed to a comparator 72 via its input 72a. Comparator 72 includes a second input 72b connected to a predetermined bias so as to detect a predetermined fiducial or reference point in the received signal. In the example illustrated in FIG. 7, this predetermined fiducial point is the "zero" cross-over point of the received signal; therefore, input 72b is at a zero-bias. Other reference points could also be used as the fiducial point, such as the maximum or minimum peak of the received signals.

The output of comparator 72 is fed to an amplifier, e.g., a monostable oscillator, 73 which is triggered to produce an output pulse at each fiducial point (zero cross-over point) in the signals received by the receiver 15. The outputs from amplifier 73 are fed via an OR-gate 74 to drive the transmitter 14 to transmit the next sonic pulse. Since a switch 71 is open transmitter 14 will thus be triggered by each signal received by the receiver 15 to transmit the next sonic pulse in the succession of pulses.

It will thus be seen that the frequency of the output pulses or signals from transmitter 14 will change with a change in the distance to the target point (the inner face 13a of displaceable sensor 13). It will also be seen that the number of wavelengths or pulses in the signal transmitted by transmitter 14, and reflected back to receiver 15, will be a whole integer. This is because the transmitter 14 transmissions are controlled by the fiducial points (zero cross-over points) of the signals received by receiver 15. This change in frequency by the transmitter 14 while maintaining the number of waves between the transmitter and receiver to be a whole integer, enables a precise determination to be made of the distance to the target point.

Thus, as known: F=C/λ, where F and C are the frequency and velocity, respectively, of the cyclically-repeating energy wave in the respective medium; and λ is the wavelength. For example, if the energy wave is a sonic wave, and the medium is air under normal temperatures and pressures, C=340,000 mm/sec; accordingly, if F=34 kHz, then λ=10 mm.

For example, if the initial transit path ABC (FIG. 7) is 100 mm, it will be seen that the number of wavelengths (pulses) in this transit path will be 10. Now, if the transit distance ATB is increased by 1 mm, i.e., from 100 mm to 101 mm, the transit time to traverse distance ATB will be correspondingly increased. However, since the frequency of transmitter 14 is controlled by the fiducial point of the signals received by receiver 15, the transmitter 14 will still produce the same number of wavelengths (pulses) during this slightly increased transit time, and therefore the wavelengths will be slightly increased in length. Thus, the increased wavelength will be 101/10=10.1 mm. The frequency of transmitter 14 will therefore be changed from 34 kHz to 340,000/10.1=33.663 kHz.

The frequency is thus decreased by 337 Hz when the distance is increased by 1 mm. Such a frequency change can be easily measured.

However, if the distance is changed by 0.001 mm (1 micron rather than 1 mm), the frequency change will be 0.337 Hz, which would be extremely difficult, if possible at all, to measure in a practical manner. Such a small frequency change can be easily measured in the system illustrated in FIG. 6 by including a summing circuit which continuously sums the measured frequency changes over a predetermined time, e.g., 100, 1,000, 10,000, or more cycles, and produces periodic readouts of the summed change.

Thus, the zero cross-over points detected in comparator 72, which are used for controlling the frequency of the transmitter 14, are also fed to a counter 75 to be counted "E" times, and the output is fed to another counter 76 controlled by a clock 77. Counter 76 produces an output to a microprocessor 78 which performs the computations according to the displacement to be detected or measured. The outputs from microprocessor 78 include a display 78a, an alarm 78b, and/or a control 78c, corresponding to outputs 19a, 19b and 19c in FIG. 1.

The following example will illustrate the high precision capability of the described system.

Assuming that the initial transit distance ABC is 136 mm, and that the initial frequency (of source 70) is 500 kHz, the initial wavelength (λ) will be 34,000/50,000, or 0.68 mm; thus initially there will be 136/0.68, or 200 wavelengths in the transit path ABC.

If this transit distance ABC is increased by 1 micron, to 136.001 mm, the number of wavelengths will remain the same (200) as described above. Therefore, the wavelength will be increased from 0.68 mm to 0.680005 mm (136.001/200); and the frequency of transmission by transmitter 14 will be decreased from 500 kHz to 499.9963236 kHz.

Assuming that clock 77 is a 500 MHz clock, the value outputted by counter 76 before the distance change will be 500·106/500·103, or 1000.

After the distance change, the frequency of the transmitter 14 will be changed from 500 kHz to 499.996 kHz (340,000/0.680005).

The value of the counter for one clock period of 550 kHz will therefore be 1,000.0073 (500 MHz/499.996 kHz), or 0.0073 Hz difference from the initial frequency. The frequency difference of 0.0073 Hz is not measurable in a practical manner.

However, if the summation factor "N" of counter 75 is selected to be 1,000, this difference of 0.0073 is multiplied by 1,000, so that the difference now becomes 7.3 Hz, which is measurable in a practical matter. If "N" of counter 75 is selected to be 10,000, then this value of 0.0073 is multiplied by 10,000, so that the frequency difference now becomes 73 Hz, which is even more precisely measurable in a practical manner.

The summation factor "N" can be determined according to the number of readouts/second required for any particularly application. For example, if 100 readouts/second are required, (i.e., a readout every 10 ms), "N" of counter 75 could be selected to be 5,000, whereupon the 0.0073 Hz frequency difference per run would be multiplied by 5,000, so as to be 36.5 Hz. It will thus be seen that the precision of the measurement can be preset almost without limitation by the selection of the appropriate clock rate for clock 77, and summation factor "N" for counter 76.

Further details as to the structure, operation and advantages of the electrical system illustrated in FIG. 6 are available in my above-cited International Applications, the contents of which are incorporated herein by reference.

FIGS. 8–14 illustrate several medical applications of the described apparatus.

Figure 8:
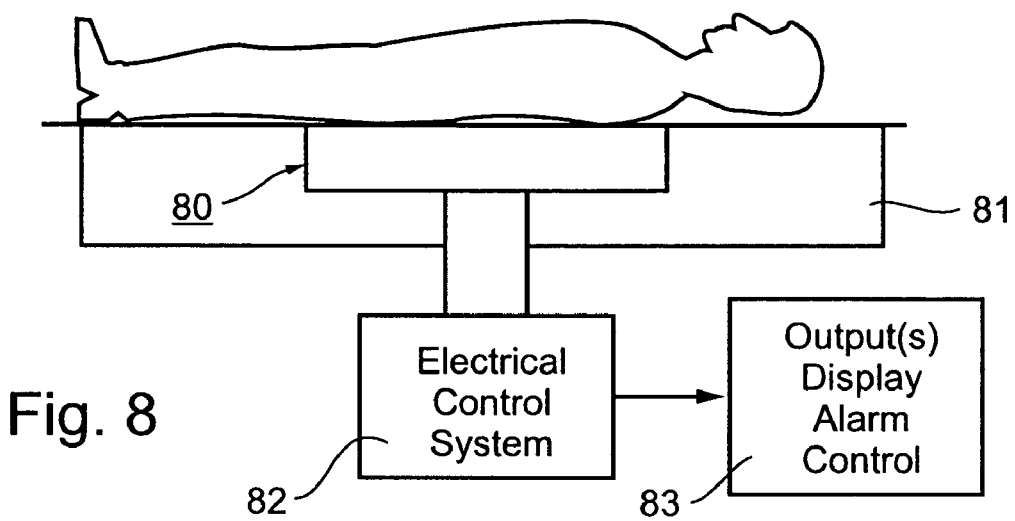
FIG. 8 is a diagram illustrating the application of the probe and measuring apparatus to a mattress, pad, or the like for measuring displacements accompanying movement of an infant or other person in order to detect apnea, to prevent bedsores, to monitor respiration or pulse rate, etc.

FIG. 8 illustrates the probe, generally designated 80, as included within a mattress 81 to be occupied by a person in order to detect movements of the person, e.g., to alert for the possibility of apnea or the development of a bedsore, to monitor respiration or pulse, etc. Thus, probe 80 is connected to an electrical control system 82, such as described above with respect to FIG. 7, which produces an output 83 for display, alarm and/or control purposes, as described above with respect to FIG. 1. The system is capable of such high sensitivity to detect respiration and heart rate even when the probe 80 is under the mattress 81.

Figure 9:
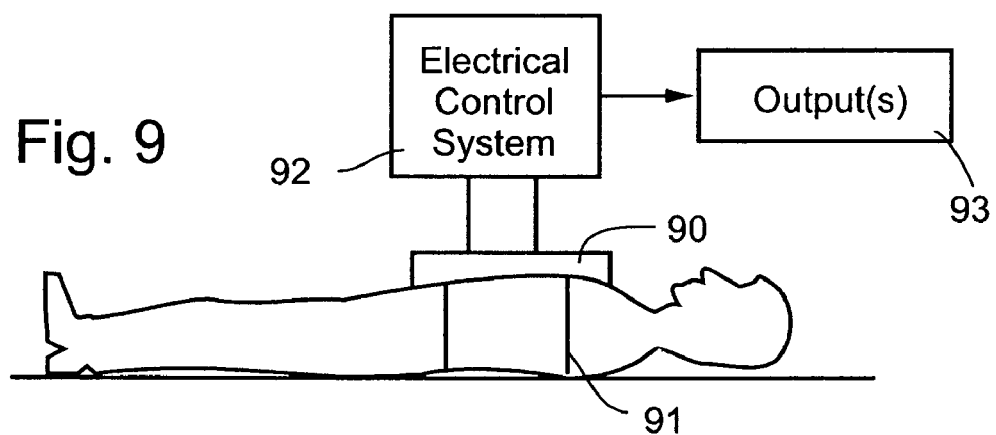
FIG. 9 illustrates the probe applied to the chest of a person for detecting and measuring displacements accompanying respiration.

FIG. 9 illustrates the application of the probe, generally designated 90, to the chest of a person by means of a harness including straps 91 or the like, to detect displacements accompanying the normal breathing or heart activity of the person. Such an application could also be used for monitoring the breathing or heart activity of the person during sleep, a surgical operation, or the like. The electrical control system 92 connected to the probe 90, which is preferably as described above with respect to FIG. 7, produces one or more outputs 93 which can be used for display, alarm and/or control purposes as described above.

It will be appreciated that the probe could also be applied over, within, or under a chair-pad, mattress or pillow to detect various respiratory or cardiovascular conditions of persons in contact therewith. Where the probe is used for monitoring breathing, it may be desired to indicate the onset of asthma; and where the probe is used for monitoring movements, it may be desired to indicate seizures.

Figure 10:
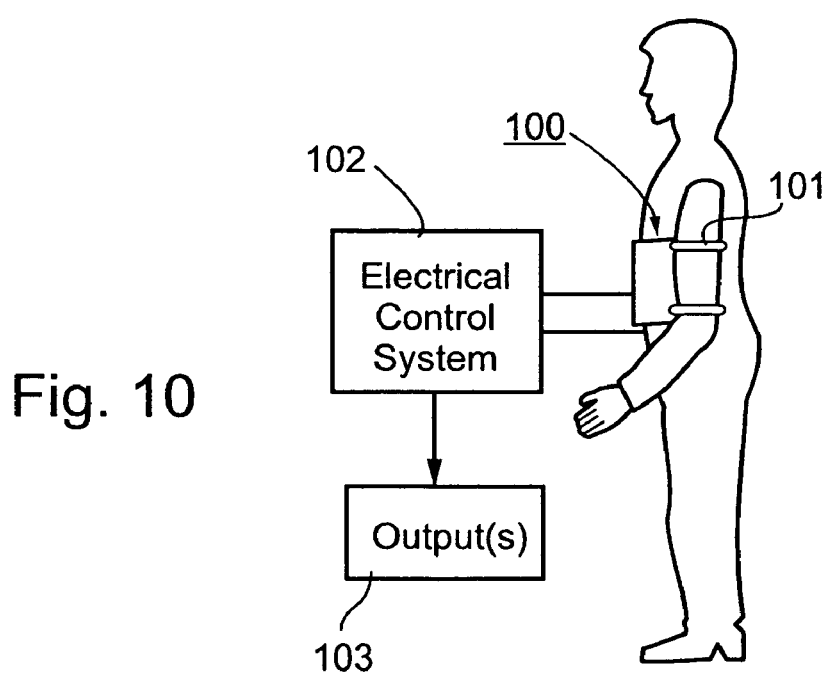
FIG. 10 illustrates the probe applied to the arm of a person for detecting and measuring a cardiovascular condition of the person, such as the pulse-rate, blood pressure, cardiac output, etc.

FIG. 10 illustrates the probe, generally designated 100, for use in detecting displacements accompanying a cardiovascular condition of a person. In the example illustrated in FIG. 10, the probe 100 is applied by a cuff 101 to the arm of the person such that the displaceable sensor of the probe is displaceable with changes in the blood flow through an artery, in order to monitor pulse-rate, blood pressure, cardiac output, or other cardiovascular condition. In this case, the outputs 103 of the electrical control system 102 connected to the probe 100 may also be used for display, alarm and/or control purposes as described above.

Figure 11:
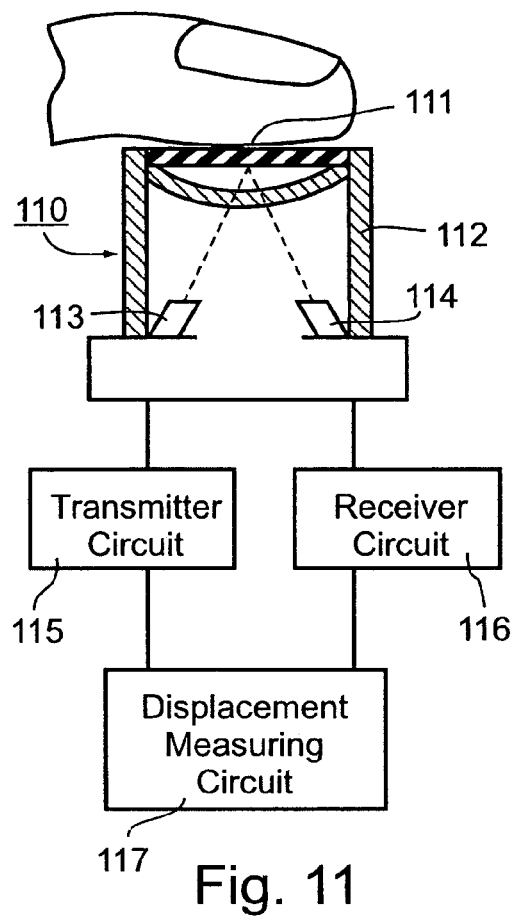

FIG. 11 illustrates the invention embodied in a finger probe 100 including a membrane 101 supported on a housing 112. When the user places a finger on the outer face of the membrane 111, the membrane will be displaced, (i.e., deformed) according to the pulsatile blood flow through the finger. The probe includes a sonic pulse transmitter 113, and a sonic pulse receiver 114, respectively controlled by transmitter circuit 115 and receiver circuit 116, and a displacement measuring circuit 117, for measuring the displacements of the inner face of the membrane 111 in the manner described above. The finger probe illustrated in FIG. 11 can thus be used for measuring the pulse rate and possibly other cardiovascular conditions, of the user.

Figure 12:
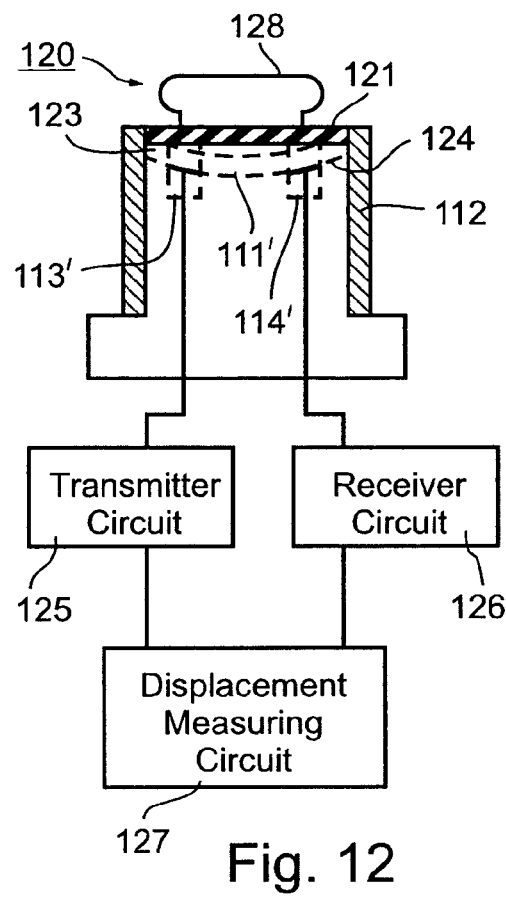
FIG. 12 illustrates another construction of probe also for measuring pulse rate, respiration rate, etc.

FIG. 12 illustrates a finger probe similar to that of FIG. 10, except that, whereas in FIG. 11 the displacement of the membrane is measured by the change in its form, particularly by the change in the transit time for the echo to be received by the receiver 104 after being reflected from the inner face of the membrane, in FIG. 12 the displacement or deformation of the membrane 121, is measured as described in FIG. 6, by the change in its length, which thereby changes the transit time for the sonic pulse to traverse the membrane 121 itself, from the transmitter 123 to the receiver 124 at two different locations on the membrane. Since the deformation of the membrane 122 increases the transit distance of the sonic pulse from the transmitter 123 to the receiver 124, the transit time will thus be increased when membrane 121 is deformed, and therefore a precise measurement may be made of the deformation of the membrane.

The probe illustrated in FIG. 12 optionally includes a button 128 engageable by the user's finger or other body part whose displacement is to be measured. Button is mechanically coupled to the membrane 122 for displacing the membrane, e.g., in response to the pulsatile blood flow through the user's finger. In all other respects, the probe 120 illustrated in FIG. 12 is constructed and operates in the same manner as the finger probe 100 described above with respect to FIG. 11.

Figure 13:
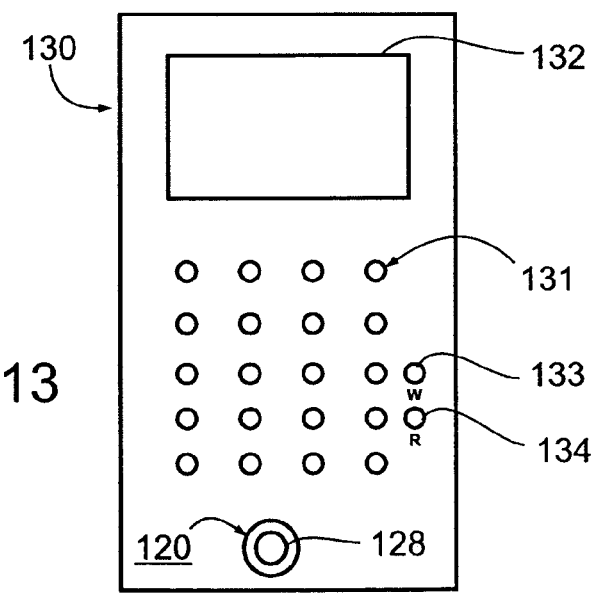
FIG. 13 illustrates the probe of either FIG. 11 or of FIG. 12 incorporated in a portable wireless communication device, particularly a cellular telephone handset, to enable the user to conveniently monitor pulse rate, respiration rate, or the like, as well as to measure a walking or running distance traversed by a user, as will be described more particularly below.

FIG. 13 illustrates a probe, such as shown in FIG. 12, incorporated into a handset of a wireless communication device, generally designated 130. In this example, the wireless communication device 130 is a cellular telephone handset, including a conventional keyboard 131 and a display 132.

Incorporating the probe 130 into such a wireless communication device provides a number of important advantages: It enables users equipped with cellular telephone handsets also to use the same handset for measuring various physiological conditions of the user, such as pulse rate and respiration rate. For example, the user may detect pulse rate by merely applying the user's finger to the button 128 coupled to the membrane 121 (FIG. 12), or by applying the button 128 to the user's wrist or to another pressure point on the user's body. The user may also measure respiration by contacting the user's chest with the button 128. The electrical circuitry within the handset would include the above-described circuitry for measuring displacement, which measurements could be displayed on the display 132. Another advantage in the probe illustrated in FIG. 13 is that the measurements of pulse rate, respiration rate, etc., may be transmitted, via the telephone, to remote locations for viewing, consultation, further processing, storage, or the like.

A further possible application of the handset illustrated in FIG. 13 is as a pedometer. Thus, the acceleration and deceleration of the displaceable sensor (e.g., membrane 121, FIG. 12) during walking or running will produce sufficient displacement or deformation of the membrane to enable the measuring system to identify the steps made by the user, and thereby to measure the distance traversed by the user. For example, the handset 130 could be pre-calibrated, by using the keys 131, for the distance traversed by the respective user during a walking step and also during a running step, and the handset could include mode selector keys, such as shown at 133 and 134, for selecting a walking (W) mode or a running (R) mode, respectively, so that by accumulating the count of running or walking steps traversed by the user, the handset would provide a measurement of the total distance traversed by the user.

While FIG. 13 illustrates the probe included in a telephone handset, it will be appreciated that it could be included in other types of portable electrical devices, such as PDAs, or the like.

Figure 14:
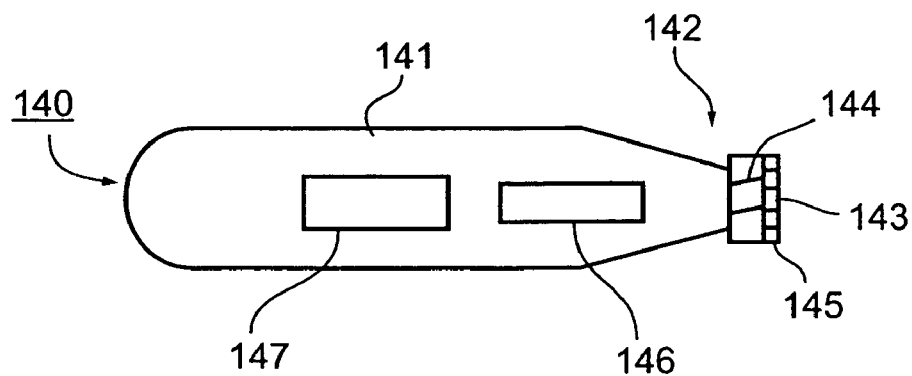
FIG. 14 illustrates a manual probe for detecting pulsatile flow, e.g., in order to identify an artery during a surgical operation.

FIG. 14 illustrates the invention embodied in a hand-held probe, generally designated 140, for conveniently detecting pulsatile flow, such as for quickly identifying an artery during a surgical operation. The probe illustrated in FIG. 14, therein generally designated 140, includes a handle 141 manually graspable by the user, and carrying at its tip 142 a displaceable sensor 143, e.g., a deformable membrane such as described above with respect to FIG. 11 or FIG. 12. Probe 140 further includes a transmitter 142 coupled to one location of the membrane 143, and receiver 145 coupled to a second location on the membrane, so that any deformation of the membrane will change the transit distances, and thereby the transit time between the pulses from the transmitter to the receiver. This transit time is measured as described above by a circuit housed within the probe, as shown schematically at 146, and the deformation of the membrane 143 can be displayed on a display 147 also carried by the probe.

Figure 15:
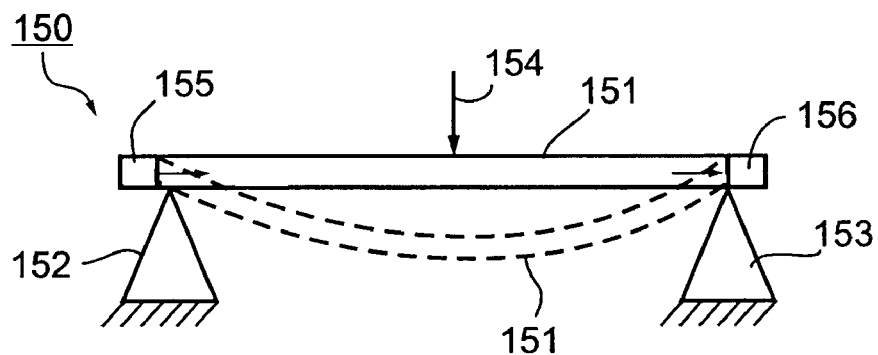
FIG. 15 illustrates the invention embodied in a strain gauge or load cell for measuring mechanical forces, such as strain, stress, torque, loads or weights.

While the invention is particularly useful in medical applications, some of which are described above, the invention is also useful in many non-medical applications. FIG. 15 illustrates one such non-medical application, namely in a strain gauge or load cell for measuring various mechanical forces, such as strain, stress, torque, load, or weight.

For purposes of example, FIG. 15 illustrates a strain gauge, generally designated 150, of the beam type, namely one having a beam 151 fixed at its opposite ends 152, 153 and adapted to receive a load 154 at an intermediate point thereof. Beam 151 carries a sonic transmitter 155 at one location thereon, and a receiver 156 at another location thereon, so that deformation or deflection of the beam 151 by the load 154 will increase the effected length of the beam, and thereby the transit distance between the transmitter 154 and the receiver 155, such that the load may be accurately measured.

In the above-described preferred embodiments, the working distance between the transmitter and receiver is at least one wavelength, and preferably more than one wavelength. If the energy source is an electromagnetic wave of, e.g., 1 MHz, this would require a minimum working distance of 300 M; and if the energy source is a sonic wave with the same frequency in metal, this would require a working distance of at least 5 mm. The invention, however, can be used with smaller working distances in both cases by providing a delay line which adds a "virtual distance" to the energy path. Thus, at 1 MHz, electromagnetic waves may be used with working distances of less than 300 M, and sonic waves may used with working distances of less than 5 mm, by merely adding an additional delay line, e.g., an ultrasonic delay line, in the feedback loop. This technique is illustrated in FIGS. 16 and 17.

Figure 16:
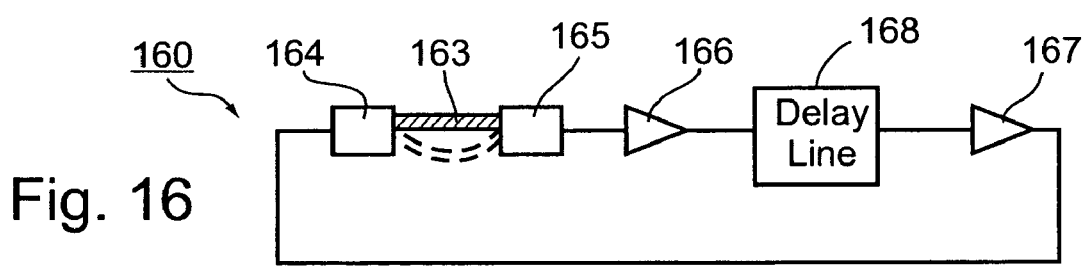
FIGS. 16 and 17 schematically illustrate one manner of implementing the invention for detecting or measuring deformations and physical movements, respectively, where the working space between the transmitter and receiver is very small, less than one wavelength.

Thus, FIG. 16 illustrates a measurement system 160 in which the displaceable sensor 163 is of the deformable change in length type so that the transit distance is changed between the transmitter 164 and receiver 165 through the displaceable sensor upon its deformation. As described particularly in FIG. 7, the output of the receiver 165 is fed through a feed back circuit including a comparator 166 (corresponding to comparator 72 in FIG. 7), and an amplifier 167 (corresponding to amplifier 73 in FIG. 7) to trigger the transmitter 164 when a predetermined fiducial point (e.g., the zero cross-over point) is detected in the received signal. In this case, however, the feedback circuit includes delay line 168, which adds a "virtual distance" to the energy path between the transmitter and receiver, thereby enabling the working distance between the transmitter and receiver to be extremely small, less than one wavelength.

Figure 17:
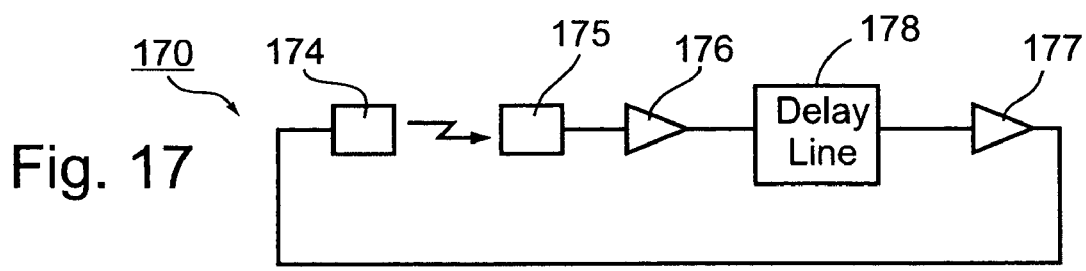

FIG. 17 illustrates a system 170 similar to that described in FIG. 16, except that physical displacements (i.e., changes in location), rather than deformational displacements (i.e., changes in length), are detected. Thus, the system 170 illustrated in FIG. 17 illustrates a transmitter 174 coupled to the receiver 175 by a space gap, so that the receiver receives the reflected or echo of the transmitted signal. The system in FIG. 17 is otherwise the same as in FIG. 16, and also includes a feedback circuit for triggering the transmitter 174, which feedback circuit includes a comparator 176, a delay line 178, and an amplifier 177, corresponding to elements 166, 167 and 168 in FIG. 16.

In an echo-detection system, such as described above with respect to FIG. 17, many obstacles may be present which produce the reflections, e.g., reflections from tissues of the human body. In such case, a "time window" may be used in order to close the feedback after each transmission, so that the signals received by the receiver will only be those from objects of interest. Thus, reflections from objects not of interest within the "window" will be ignored.

Figure 18:
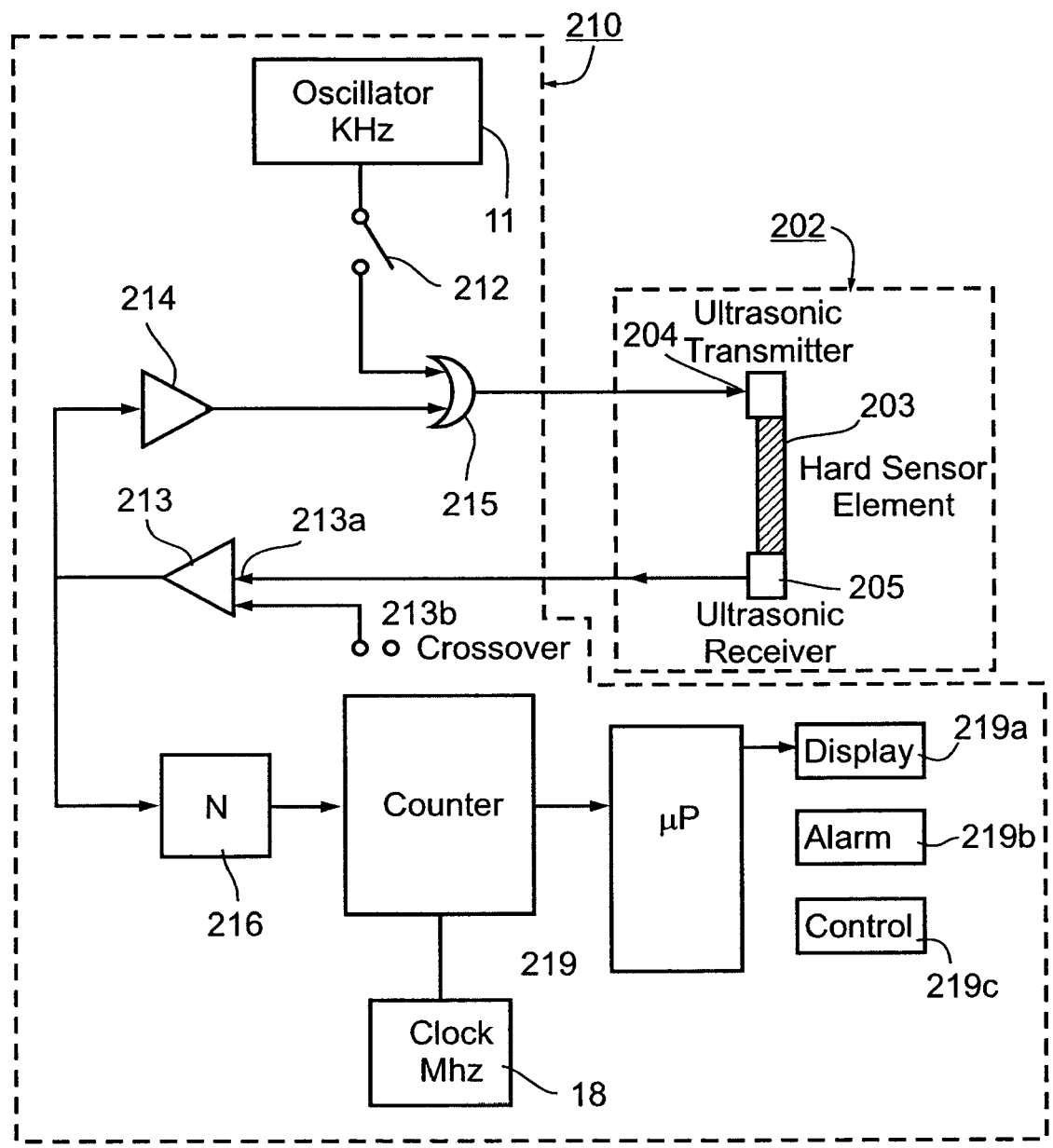
FIG. 18 is a block diagram illustrating one form of temperature measuring apparatus constructed in accordance with the present invention.

FIG. 18 illustrates apparatus which includes a probe, generally designated 202, for measuring temperature with a high degree of accuracy. Probe 202 includes a heat-sensor element 203 which is to be exposed to the temperature to be measured, and which undergoes a predeterminable change in length in response to such temperature. Probe 202 further includes a transmitter 204 for transmitting a succession of energy pulses, in this case sonic pulses, through the heat-sensor element 203 from a first location of the element towards a second location thereof, in this case from one end to the opposite end of the heat-sensor element; and a receiver 205 for receiving the energy pulses at the second location of the heat-sensor element. The transmitter 204 and receiver 205 are electrically connected to a data processor system, generally indicated by the broken-line block 210, which drives the ultrasonic transmitter 204 and computes the transit time between the transmission and the reception of the sonic pulses. Data processor system 210 utilizes the measured transit times to produce a measurement of the temperature of the heat-sensor element 203, and thereby of the body or environment to which the heat-sensor element is exposed.

Data processor system 210 is generally constructed as described in FIG. 7 and in the above-cited International Applications. Briefly, it controls the transmitter 204 to transmit a succession of sonic pulses from one end of the heat-sensor element 203 through that element, while the receiver 205 receives the sonic pulses from the opposite end of the heat-sensor element 203. Data processor 210 detects a predetermined fiducial point of each received sonic pulse and utilizes the detected fiducial point to trigger the transmitter 204 to transmit the next sonic pulse in the succession. The data processor determines the frequency of transmission of the sonic pulses in the succession, and utilizes the latter determination to produce a measurement of the transit time of the sonic pulses through the heat-sensor element 203.

The measured transit time is affected by the length of the path of the sonic pulses from the transmitter to the receiver. This in turn depends on the temperature of the heat-sensor element since that element undergoes a predeterminable change in length in response to temperature. The transit time also depends on the velocity of transmission of the sonic pulse through the heat-sensor element, which also varies in response to temperature in a predeterminable manner. The above-cited International Applications describe in particular how the system illustrated in FIG. 18 measures the transit time of the sonic pulses with a very high degree of precision, which thereby enables the temperature of the heat-sensor element to be determined also with a very high degree of precision.

The apparatus illustrated in FIG. 18 operates as follows: Initially, a succession of sonic pulses are continuously transmitted by transmitter 204 as driven by oscillator 211, (switch 212 being closed) until the pulses through the heat-sensor element 203 are received by receiver 205. Once the pulses are received, switch 212 is opened so that the received pulses are thereafter used for controlling the transmitter 204.

As shown in FIG. 18, the pulses received by receiver 205 are fed to a comparator 213 via its input 213a. Comparator 213 includes a second input 213b connected to a predetermined bias so as to detect a predetermined fiducial or reference point in the received signal. In the example illustrated in FIG. 18, this predetermined fiducial point is the "zero" cross-over point of the received signal; therefore, input 213b is at a zero-bias. Other reference points could also be used as the fiducial point, such as the maximum or minimum peak of the received signals.

The output of comparator 213 is fed to an amplifier or monostable oscillator 214 which is triggered to produce an output signal at each fiducial point (zero cross-over point) in the signals received by the receiver 205. The signals from amplifier 214 are fed via an OR-gate 215 to trigger the transmitter 204 to transmit the next sonic pulse.

Accordingly, once switch 212 is opened, the transmitter 204 will thereafter be triggered by each signal received by the receiver 205 to transmit the next sonic pulse in the succession of pulses, the triggering of the transmitter being effected by detecting the predetermined fiducial point in each signal received by receiver 205.

It will thus be seen that the frequency of the transmitter 204 will change with a change in the length of (and also signal velocity through) the heat-sensor element 203 (both of which are known or predeterminable); and that the number of wavelengths or pulses in the signal transmitted by the transmitter 204 and received by the receiver 205 will be a whole integer. This measurement of the change in frequency by the transmitter, while maintaining the number of waves between the transmitter and receiver as a whole integer, enables a precise determination to be made of the transit distance of the pulse through the heat-sensor element 203, and thereby the temperature of that element.

For further particulars as to the operation of the system illustrated in FIG. 18, and particularly of the manner in which extremely high precision is attainable by such a measuring system, reference may be made to the above-cited International Applications.

Figure 19:
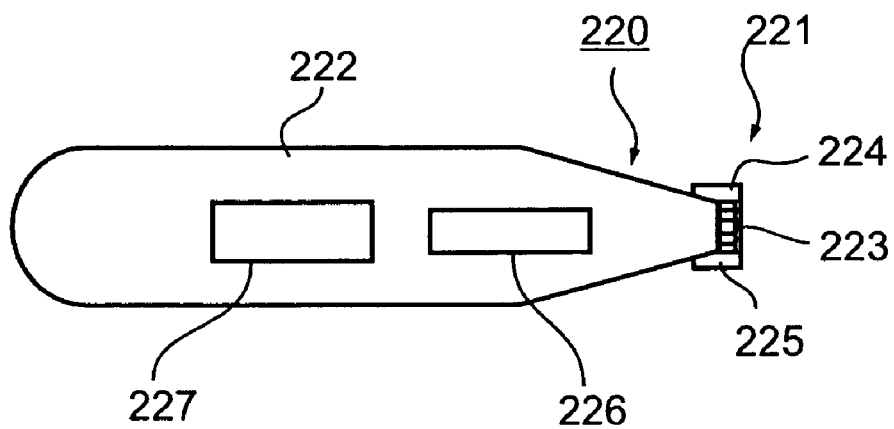
FIG. 19 illustrates a hand-held temperature-sensing probe constructed in accordance with the present invention.

FIG. 19 illustrates a probe, generally designated 220, carried at the tip 221 of a handle 222 adapted to be manually held by the user and to be placed against tissue or location where the temperature is to be measured. Tip 221 of the probe 220 thus includes a heat-sensor element 223, such as of metal, which undergoes a predetermined change in length (and signal velocity) in response to temperature. The heat-sensor element 223 is fixed to the tip 221 of the probe 220. A transmitter 224 is fixed to one end of the heat-sensor element 223, and a receiver 225 is fixed to the opposite end of element 223 so that the distance between the two (the signal transit distance) varies with the temperature of that element. As described above with respect to FIG. 18, the transmitter 224 transmits a succession of sonic pulses through the heat-sensor element 223 from one end (or other location) thereof, while the receiver 225 receives the energy pulses at the opposite end (or other location) of the heat-sensor element.

The electrical system for driving the transmitter 224, and for controlling it in response to the signals received by the receiver 225, is carried by a unit 226 housed within the handle 222. Unit 226 also includes the data processor described above with respect to FIG. 18 for computing the transit time between the transmission and the reception of the sonic pulses, and for utilizing the measured transit times to produce a measurement of the temperature of the heat-sensor element 223.

The probe illustrated in FIG. 19 may thus be applied to any body part, body tissue, or other location, in order to accurately measure the temperature of such body part, tissue, or location. The measured temperature may be displayed on a display 227 also carried by handle 222. Such a probe may thus be used not only for measuring the body temperature, but also the temperature of selected tissue, by placing the heat-sensor element 223 into contact with such tissue, for example to distinguish cancerous tissue from non-cancerous tissue.

Figure 20:
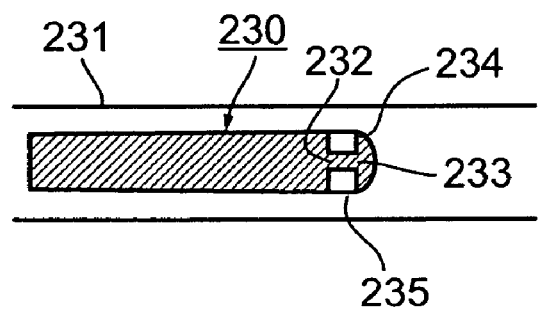
FIG. 20 illustrates a probe constructed in accordance with the present invention to be used with a catheter.

FIG. 20 illustrates a probe, generally designated 230, constructed in accordance with the present invention to be carried within a catheter insertable into a passageway 231 of a person's body for measuring temperature at any selected point therein. Probe 230 carries, at its tip 232, a heat-sensor element 33 straddled on its opposite sides by a sonic pulse transmitter 234 and a sonic pulse receiver 235 controlled by a data processor (not shown) for measuring the transit time of sonic pulses through element 233 in accordance with the above-described method. As described above, this provides a high accurate measurement of the temperature of that element, and thereby of any tissue that may be contacted by that element. Preferably, the tip of the catheter carrying the heat-sensor element 233 is curved so as to facilitate the passage of the catheter through the passageway 231. Such a catheter probe would be particularly useful for monitoring the temperature of plaque on a blood vessel (well), as the higher the temperature, the more likely the plaque will release an embolus.

Such a probe could also carry or include a deformable membrane or other type of displaceable sensor for measuring blood pressure, flow rate, etc., at selected locations in the cardiovascular system of the person.

Figure 21:
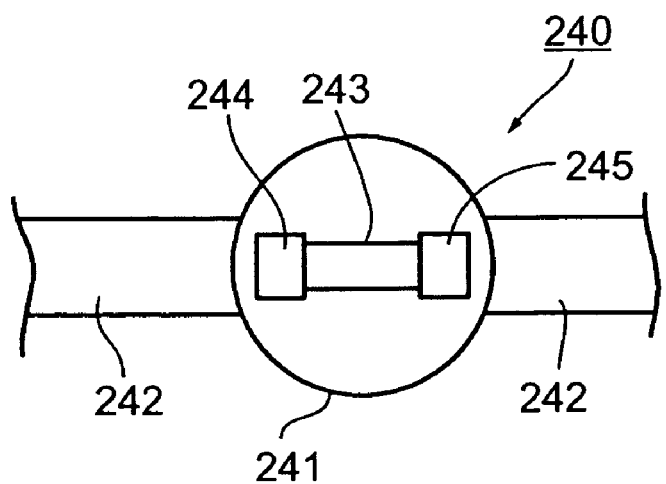
FIG. 21 illustrates a probe constructed in accordance with the present invention carried by a wristband for application around the wrist of the user to be used, for example, as a blood glucose-level detector.

FIG. 21 illustrates the invention embodied in a temperature-measuring probe 240 particularly useful for indicating the glucose level in the blood of a person. Thus, the probe is embodied in a housing 241 having a wristband 242 for application to the wrist of the user, with the inner face of housing 241 containing the heat-sensor element 243 to be brought into contact with the user's skin. The heat-sensor elements 243 includes a sonic pulse transmitter 244 and a sonic pulse receiver 245 fixed thereto at its opposite end so as to be effective, as described above, for accurately measuring the transit time of the sonic pulses through element 243, and thereby the temperature of that element, as well as the tissue contacted by that element.

Probe 240 may also be used for providing a continuous measurement of body temperature for other purposes, e.g., to detect an infection. When used for continuously indicating the blood-glucose level, it may equipped with other sensors, such as skin-conductivity sensors, which have also been found to provide an indication of blood-glucose level. The data processor housed within the probe 240 may be programmed to automatically produce an alarm when the detected blood-glucose level is found to exceed a predetermined value. The temperature sensor may also be used for automatically controlling an insulin pump in accordance with the detected glucose level as measured by the temperature sensor.

Figure 22:
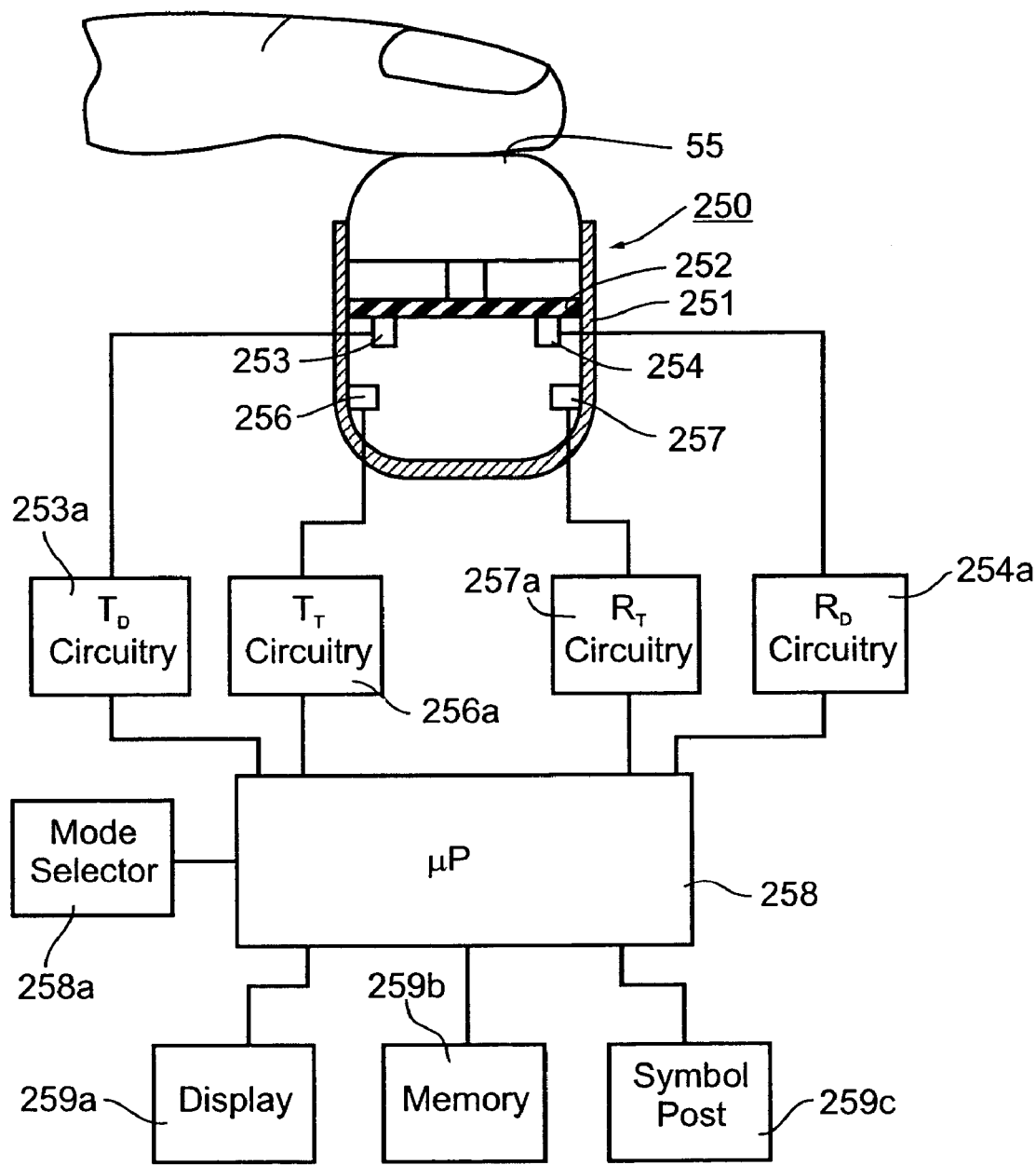
FIG. 22 illustrates a finger probe constructed in accordance with the present invention.

FIG. 22 illustrates the invention embodied in a finger probe having a heat-sensor element for measuring both temperature, and one or more other body conditions of a user.

Thus, the finger probe illustrated in FIG. 22, and therein generally designated 250, includes a housing 251 of a thermally-conductive material, such as metal, closed at its upper end by a deformable membrane 252 having a sonic pulse transmitter 253 at one location, and a sonic pulse receiver 254 at another, spaced location. Membrane 252 is coupled to a metal button 255 slidable within metal housing 251 and in good, thermal contact with the metal housing. A second sonic pulse transmitter 256 is fixed to one location of the metal housing 251, and a second sonic receiver 257 is fixed to another, spaced location of the housing.

The temperature of the user's finger may be sensed and measured by placing a finger on metal button 255. Since button 255 is in good thermal contact with the metal housing 251, the housing tends to expand or contract according to the temperature of the user's finger. Transmitter 256 fixed to the metal housing 251 is driven by a drive circuit 256a, and receiver 257 also fixed at another location to the metal housing 251 is coupled to a receiver circuit 257a. Both circuits 256a and 257a are connected to a microprocessor 258 which, by accurately measuring the change in length of the path from transmitter 256 to receiver 257 as described above, accurately measures the temperature of the user's finger as detected by the transmitter 256 and receiver 257.

Similarly, transmitter 253 and receiver 254, fixed to spaced locations on the deformable membrane 252, are also coupled to a drive circuit 253a and to a receiver circuit 254a, respectively, and to the microprocessor 258. Microprocessor 258 is thus capable of accurately measuring the deformations of the membrane 252, by the changes in the distance between the transmitter 253 and the receiver 254, in the same manner as described above.

This accurate measurement of the deformations of the membrane 252 enables the probe illustrated in FIG. 22 also to be used for detecting and measuring changes in the pulsatile blood flow through the user's finger. Such information can be used for monitoring the pulse rate of the user, as well as other cardiovascular conditions, such as blood pressure, cardiac output, etc.

The system illustrated in FIG. 22 therefore further includes a mode selector 258a which selects the mode of operation of the finger probe. Thus, if a temperature mode is selected, the transmitter 256 and receiver 257 would be effective to measure the temperature of the user's finger placed on the button 255; and if a pulse-rate (or other cardiovascular parameter) measurement mode is selected, the transmitter 253 and receiver 254 would be effective to measure the pulse rate (or other cardiovascular condition) manifested by the user's finger applied to button 255.

The apparatus illustrated in FIG. 22 further includes a display 259a for displaying the measured parameter (e.g., temperature or pulse rate), a memory 259b for storing the measured parameter, and/or an external port 259c for transmitting the measured parameter to a remote location.

Figure 23:
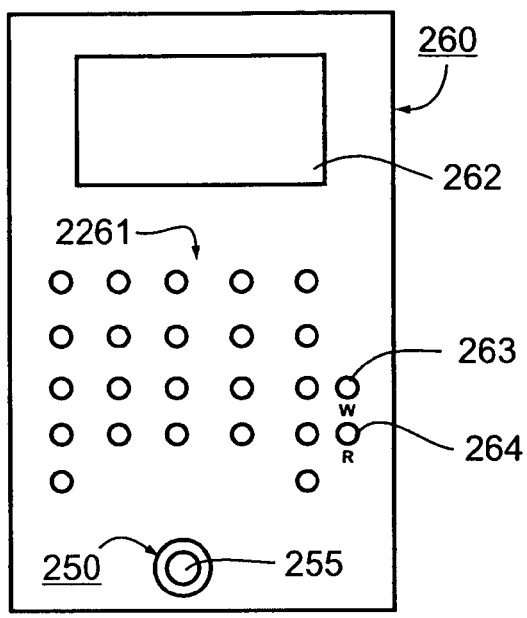
FIG. 23 illustrates a probe, such as that of FIG. 22, incorporated in a cellular telephone handset or other portable electrical device.

FIG. 23 illustrates the finger probe shown in FIG. 22 incorporated in a hand-held portable unit, e.g., a cellular telephone handset 260, as described above with respect to FIG. 13. Thus, the cellular handset 260 includes the conventional set of keys 261 and display 262, and in addition the finger probe 250, with its sensor button 255 for sensing and measuring temperature, pulse rate, etc. The unit 260 illustrated in FIG. 23 may also be used for measuring respiration rate by applying the button 255 to the user's chest. It may also be used as a pedometer for measuring distance traveled by the user. Thus, the accelerations and decelerations of the user while walking or running cause deformations in the membrane 252, which deformations are sensed and measured by its transmitter 253 and receiver 254, thereby enabling the device to record the number of steps taken by the user.

As described above with respect to FIG. 13, the user may precalibrate the data processor within the unit 260 as to the distance of each walking step and of each running step by the user, so that when the unit is carried by the user, the unit will count the number of steps and produce an accurate measurement of the distance traveled by the user while walking and while running. The keyboard of the unit 260 may include a key 263 (W) for selecting the walking mode, and another key 264 (R) for selecting the running mode, both when calibrating the unit for the distance of each walking step and running step, and also when using the unit for measuring distance traveled.

Figure 24:
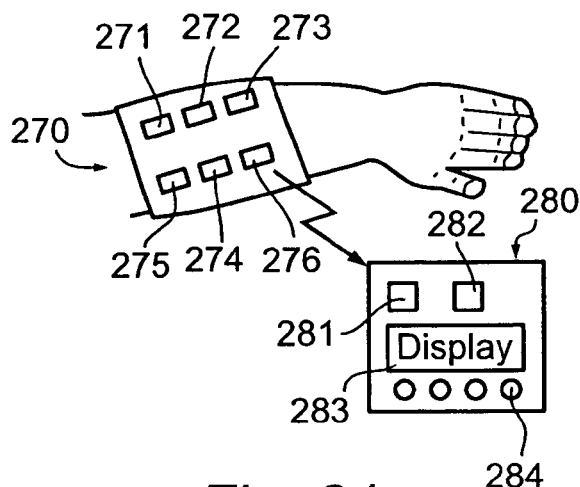
FIG. 24 illustrates one form of apparatus constructed in accordance with the invention applied to a wounded part of a person's arm, under a dressing or within a cast, to monitor the progress of healing of the wound.
Figure 25:
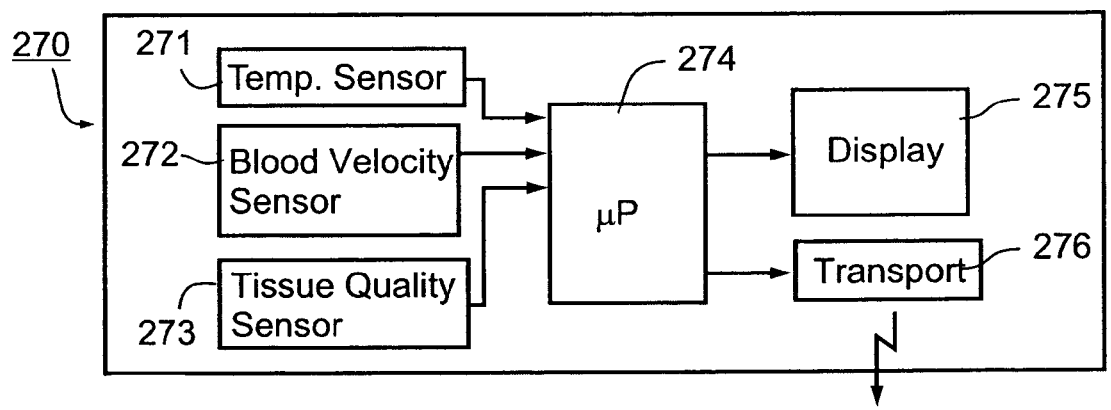
FIG. 25 is a block diagram illustrating the main components of the apparatus of FIG. 24.
Figure 25:
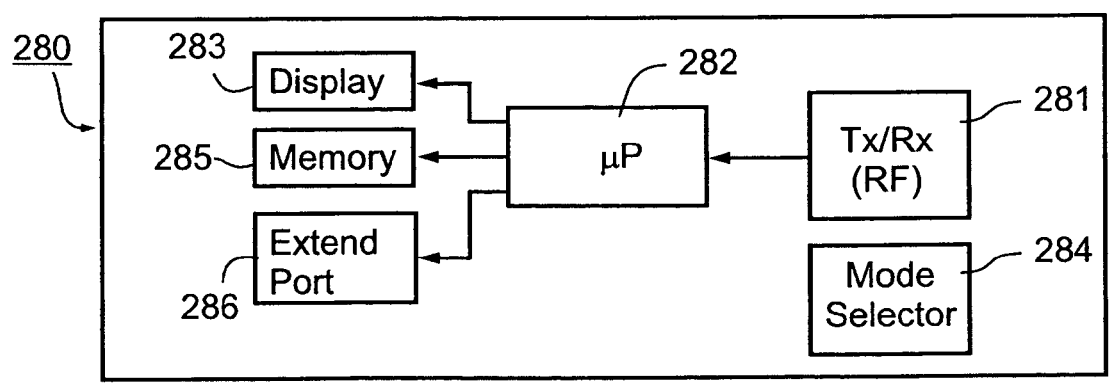

FIGS. 24 and 25 illustrate apparatus constructed in accordance with the present invention to be applied over a wound in a person's limb (e.g., a fracture), to indicate the progress of healing of the wound. The illustrated apparatus includes a sensor assembly, generally designated 270, applied over the wound, so as to sense various conditions at the wound site as described more particularly below. The sensor assembly 270 shown in FIG. 24 would be normally covered by a dressing, or incorporated in a cast, neither of which is shown in FIG. 24 to better illustrate the sensor assembly.

Thus, as shown in FIG. 24, and more particularly in FIG. 25, the sensor assembly 270 applied over the wound includes a temperature sensor 271, a blood-velocity sensor 272, and a fissue-density sensor 273. It also includes a microprocessor 274 for receiving the outputs of sensors 271, 272 and 273, and for producing measurements of the respective conditions sensed by the sensors. To enable the outputs of the sensors to be read from sensor assembly 270 itself, i.e., after removing the dressing (not shown), the sensor assembly may further include a display 275.

However, to enable the progress of healing to be monitored without removing the dressing, or the cast, the sensor assembly 270 preferably also includes a transponder unit 276 which, upon being interrogated by an external unit shown at 280 in FIG. 24, transmits the measurements made by the sensors 271, 272, 273 to the external unit 280, e.g., by wireless RF. Thus, the external unit 280 includes a transmitter/receiver 281 communicating with transponder 276; a microprocessor 282 for processing the information received by the external unit, and a display 283 for displaying such information. The external unit 280 also includes a keyboard 84 containing, among other keys, keys to enable any desired mode of operation to be selected, e.g., for measuring and displaying temperature, blood-velocity, and/or tissue-density, at the wound site. As shown in FIG. 25, the external unit further includes a memory 285 for recording the received data, and an external port 286 for enabling such data to be transmitted to a remote location for viewing, storing or further processing.

The above parameters provide information indicating the progress of healing of the wound. For example, an inflammation condition would tend to produce an increase in the temperature at the wound, an increase in the blood-velocity flow, and a decrease in the tissue density. On the other hand, a decrease in the blood velocity flow or an increase in the tissue density might indicate the onset of gangrene at the wound site. For example, a drop in temperature accompanied with reduced blood flow in a person's foot would indicate the development of gangrene, particularly where the person is diabetic.

The probe assembly 70 shown in FIG. 24 could include a matrix of temperature sensors to measure the temperatures at different regions of the wound, which information may also be useful in indicating the progress of healing of the wound.

It will be appreciated that the sensor assembly 270 illustrated in FIGS. 24 and 25 could include other sensors, for example pulsatile-flow sensors (e.g., sensed by deformation of a displaceable element), skin-conductivity sensors, oxygen-saturation sensors, or any other sensor which may provide useful information as to the progress of healing of the wound.

While any of the foregoing sensors may be conventional sensors, preferably each senses its respective parameter according to the technique described above, particularly with respect to FIG. 18 for measuring temperature.

Figure 26:
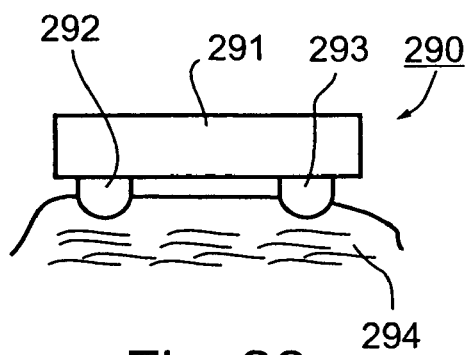
FIG. 26 schematically illustrates a probe constructed in accordance with the invention for measuring blood flow and/or tissue density, e.g., for use in the probe assembly of FIGS. 24 and 25.

FIG. 26, for example, illustrates how this basic technique may be used for detecting and measuring blood-velocity or tissue density. The sensor illustrated in FIG. 26 includes a mounting plate 291 mounting a sonic transmitter 292 at one location, and a sonic receiver 293 at another, spaced location, such as to enable the transmitter and receiver to straddle tissue, shown at 294, containing the blood flow whose velocity is to be measured or the tissue whose density is to be measured.

Figure 27:
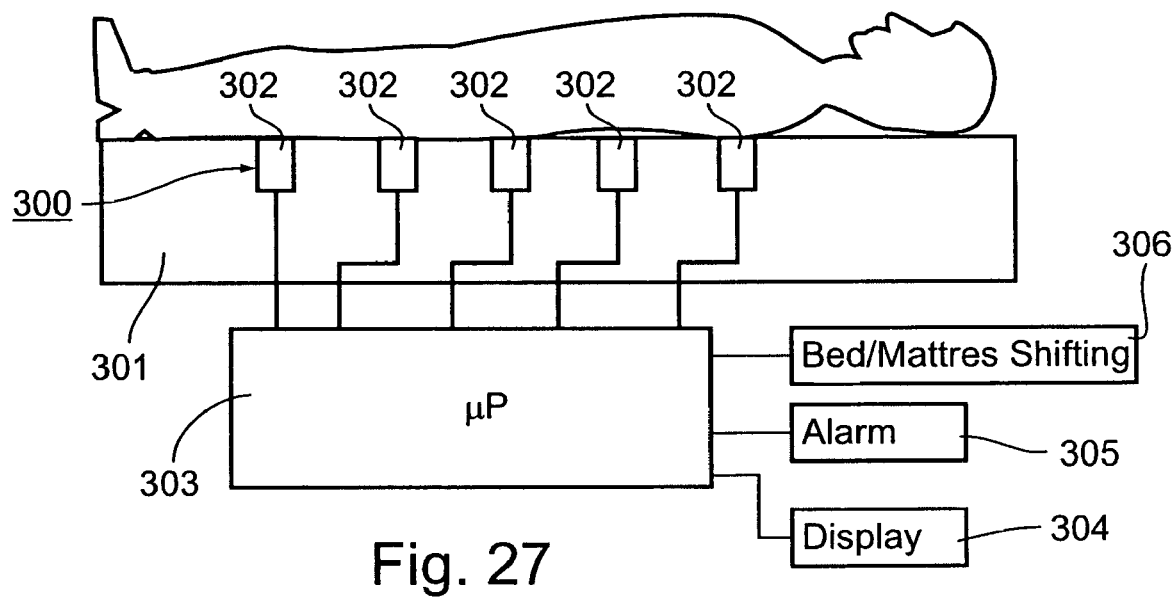
FIG. 27 diagrammatically illustrates a probe assembly constructed in accordance with the invention incorporated in a mattress to prevent the formation of bed sores.

FIG. 27 illustrates another application of the invention, wherein a probe assembly, generally designated 300, is included on, within, or under a mattress 301 for detecting bed sores. Thus, the probe assembly 300 would include a plurality of temperature sensors 302 at various locations on the mattress in order to detect unduly high temperatures at various locations of the person lying on the mattress, which could indicate the presence or onset of a bedsore at the respective location. The outputs of the temperature sensors 302 are fed to a microprocessor 303 which processes them in the manner as described above to control a display 304 or an alarm 305. The microprocessor 303 could also control an actuator device 306 which automatically shifts the mattress 301, or controls the air pressure within the mattress if of a fluid inflatable type, to prevent the formation of a bedsore as would be indicated by an unduly high temperature at the respective location.

Figure 28:
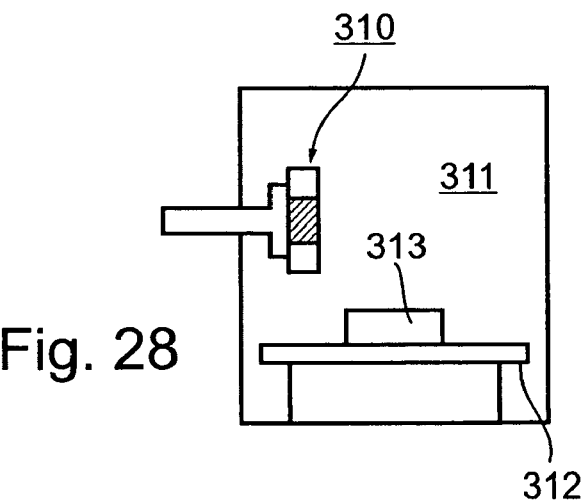
FIG. 28 illustrates a probe constructed in accordance with the present invention for insertion into a reaction chamber for measuring the temperature therein.

While the invention has been described particularly with respect to medical applications, it will be appreciated that it could be used in many non-medical applications. FIG. 28 schematically illustrates one such non-medical application, namely for measuring and/or controlling the temperature within a heated chamber used for processing work-pieces, such as semi-conductor wafers which requires very close control of the temperature during their various processing operations.

Thus, FIG. 28 illustrates the temperature probe, generally designated 310, introduced into a heated chamber 311 provided with a table 312 for supporting a wafer 313 being processed in that chamber. The temperature probe 310, constructed as described above with respect to FIG. 18, will thus provide a very accurate measurement of the temperature within chamber 311.

Figure 29:
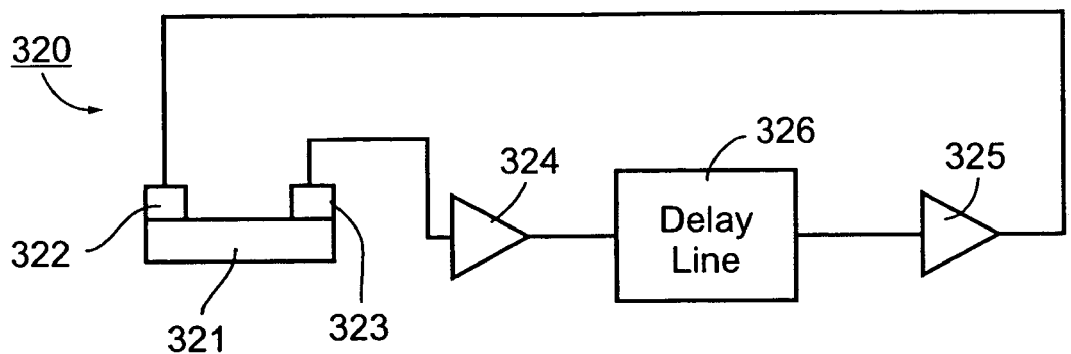
FIG. 29 schematically illustrates one manner of adding a "virtual distance" to the feedback energy path in order to enable the probe to be used with very short working distances, of less than one wavelength, between the transmitter and receiver.

FIG. 29 illustrates probe assembly constructed in accordance with the technique described above in FIG. 16 for adding a "virtual distance from the transmitter to the receiver. Thus, the probe assembly 320 therein illustrated is of the temperature-sensor type. It includes a heat-sensor element 321 having a sonic transmitter 322 fixed at one location thereof, and a sonic receiver 323 fixed at a second, spaced location thereof, so as to receive the sonic pulses from the transmitter 322 after traversing the heat-sensor element 321. As described above, receiver 323 includes a feedback circuit, comprising a comparator 324 and an amplifier 325 for triggering the transmitter 322 at each predetermined fiducial point of the signal received by the receiver 323.

In order to enable such a probe to be used in applications requiring a very small working distance between the transmitter 322 and the receiver 323, less than one wavelength, the feedback circuit illustrated in FIG. 29 includes a delay line 326 which adds a "virtual distance" to the energy path from the receiver 323 to the transmitter 322, to thereby enable the two to be spaced very close to each other, less than one wavelength.

While the technique illustrated in FIG. 29 is shown with respect to a temperature-sensor probe, it will be appreciated that the same technique can be used with respect to the tissue-density or blood-velocity probe illustrated in FIG. 26, or with respect to any parameter-measuring probes based on the same measuring technique.

In addition, where many obstacles may be present which produce the reflections (e.g., reflections from tissues of the human body), a "time window" may be used in order to close the feedback after each transmission, so that the signals received by the receiver will only be those from objects of interest. Thus, reflections from objects not of interest within the "window" will be ignored.

Figure 30:
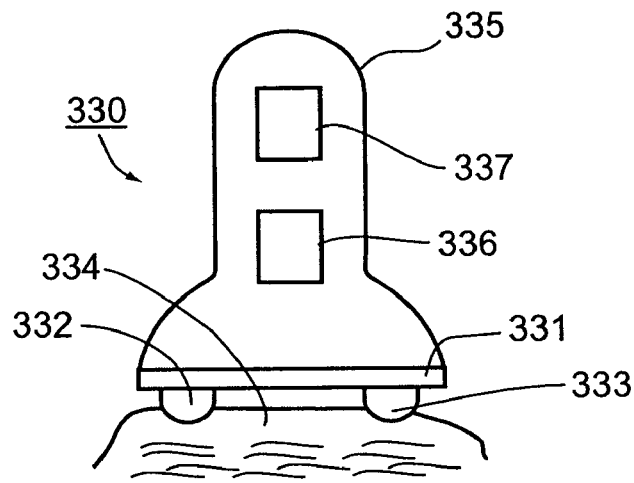
FIG. 30 illustrates a hand probe which may be used, e.g., for examining tissue in order to identify it as normal tissue or cancerous tissue during a surgical operation, as well as for many other applications as will be described more particularly below.

FIG. 30 illustrates a manual probe which may be used in many medical and non-medical applications for examining any characteristic of an object, solid, liquid or gases, which affects the transit time of an energy pulse, sonic or electromagnet, from a transmitter to a receiver. For purposes of example, the probe illustrated in FIG. 30 is shown for use in examining tissue in a real-time manner, e.g., during a surgical operation, in order to characterize the examined tissue as being normal, healthy tissue, or cancerous tissue.

It will be appreciated that identifying certain tissue as normal or cancerous can be very critical in a surgical operation to assure that all the cancerous tissue was removed with a minimum of normal, healthy tissue. It has long been known that cancerous tissue differs in certain characteristic from normal, healthy tissue. Many techniques have been described in the literature for examining a number of such characteristics, such as electrical conductivity, electrical impedance, and tissue density in order to identify the tissue as normal or cancerous, but such techniques have not yet proved satisfactory probably because of the lack of sufficient accuracy and/or spatial resolution to enable them to be used in real time during a surgical operation.

The probe illustrated in FIG. 30, and therein generally designated 330, is constructed similarly to that illustrated in FIG. 26. Thus, it includes a mounting member 331 which mounts a transmitter 332 and a receiver 333 in spaced relationship to enable them to straddle the object, in this case tissue 334, to be examined. The manual probe in FIG. 30 further includes a handle 335 which houses the electrical circuitry 336 used in the measurement, e.g., as shown in FIG. 18, and also a display 337 to display the results of the measurements.

As described above, the measurement system can produce extremely high accuracy, as desired, with respect to the characteristic measured, (e.g., which may be an electrical property such electrical conductivity or impedance, or a physical property such as tissue density) in order to compare the measured characteristic with the corresponding characteristics of normal tissue and cancerous tissue, and thereby to identify the tissue as either normal or cancerous. In addition, the spatial resolution can also be selected as desired by appropriately selecting the wavelength of the energy source used in the transmitter 332 (electromagnetic or sonic), and/or by introducing a delay line in the feedback circuit as described above with respect to FIG. 29 in order to introduce a "virtual distance" to the "working distance" between the transmitter and receiver.

A probe as illustrated for example in FIG. 30 may be used for examining other characteristics of other objects. For example, by applying the probe to straddle a conduit for a liquid or gas, the flow of velocity, composition, viscosity, temperature, etc. of the flowing liquid or gas may be determined.

Figure 31:
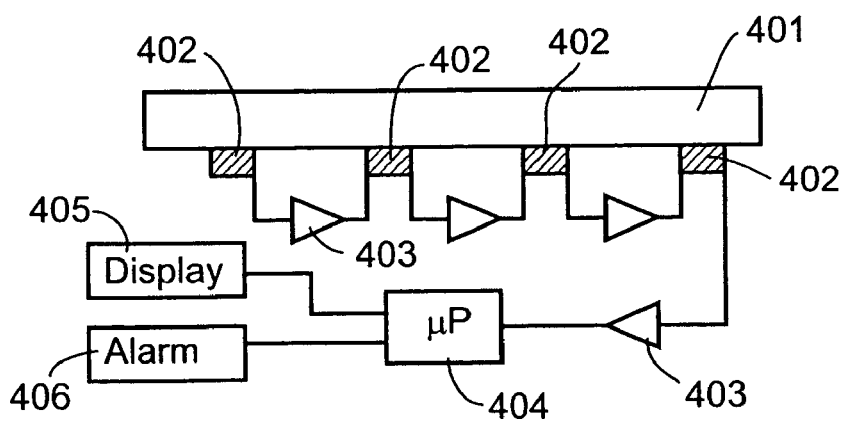
FIG. 31 diagrammatically illustrates another probe assembly incorporated in a mattress in order to detect apnea, to prevent bedsores, or to monitor another medical condition of an occupant of the mattress, such as respiration, pulse rate, etc.

FIG. 31 illustrates a still further application of the invention, wherein a probe assembly, generally designated 400, is included on, within or under a mattress 401 for detecting apnea, bed sores, respiration rate, blood pulse rate, etc., of the occupant of the mattress. Thus, probe assembly 400 illustrated in FIG. 31 includes a plurality of displaceable sensors 402 at various locations with respect to the mattress 401, all the sensors being connected in series via amplifiers 403 to a microprocessor 404, which controls a display 405, an alarm 406, or other output device.

Figure 32:
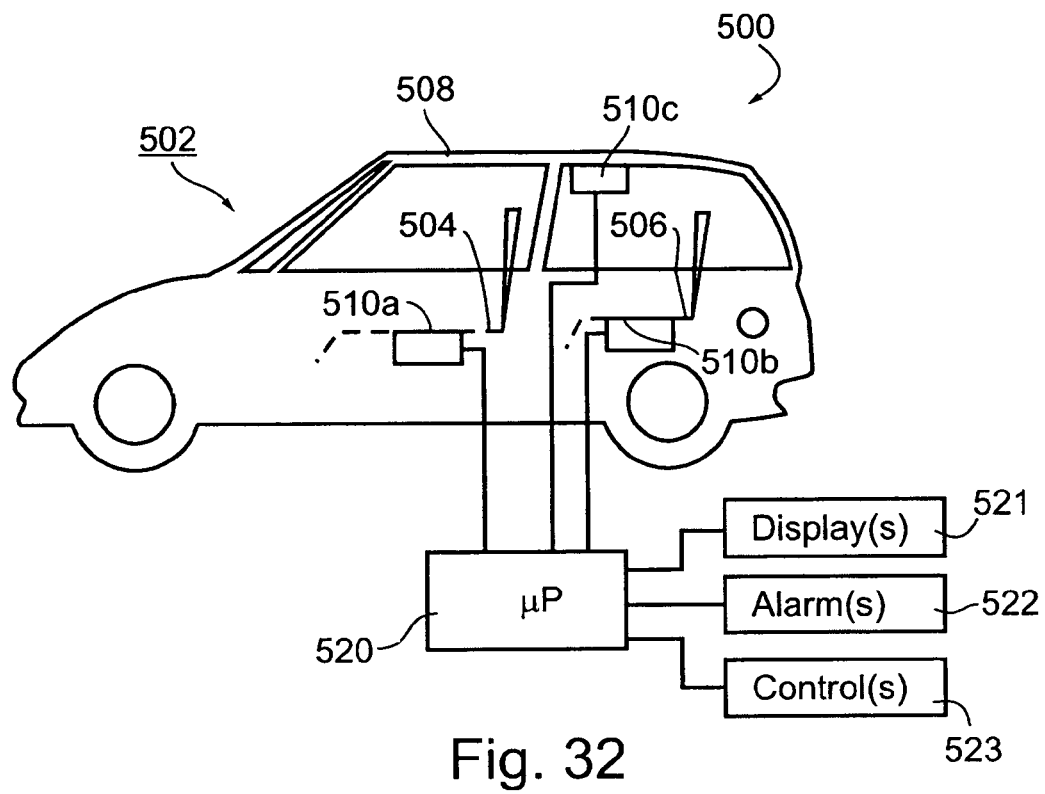
FIG. 32 diagrammatically illustrates implementations of the invention for producing high-precision measurements regarding occupants of a motor vehicle, and/or for detecting intrusions by unauthorized persons into a motor vehicle.

FIG. 32 illustrates the invention implemented in a motor vehicle for producing high-precision measurements regarding occupants of the vehicle, and/or for detecting intrusions by unauthorized persons into the vehicle.

Thus, FIG. 32 illustrates a motor vehicle, generally designated 502, having a front seat 504 equipped with the novel probe 510a to sense various conditions, to be described below, of the driver or other occupant of the front seat. The rear seat 566 of the vehicle 502 is also equipped with the novel probe 510b also to sense various conditions of an occupant of the rear seat, as will be described below. Vehicle 502 illustrated in FIG. 32 includes a third probe 510c, e.g., attached to the inside of the roof 508 of the vehicle, for monitoring the space within the vehicle, e.g., to detect movements of persons within the vehicle.

Each of the probes 510a, 510b and 510c illustrated in FIG. 32 may be and of the constructions described above. When such a probe is used as a seat probe for the driver's seat 504 as shown by probe 510a in FIG. 32, or for the rear seat 506 as shown by probe 510b in FIG. 32, the membrane (FIG. 13, FIG. 1) will be displaced according to certain conditions, as described below, of the occupant of the front seat 504 or rear seat 506, respectively. When the probe 510 is used as a space-monitor, as shown by probe 510c in FIG. 32, the membrane will be deformed by any movements within the interior of the vehicle 502.

The deformations of the membrane (FIG. 13, FIG. 1) of the probes 510a, 510b and 510c in the vehicle 502 illustrated in FIG. 32, are sensed and/or measured by a displacement measuring circuit, indicated by block 520 in FIG. 32, which produces outputs to various output devices, including a display 521, an alarm 522, and/or a controller 523, as described more particularly above.

Such a measuring technique is so sensitive such that, when the probe is applied to the driver's seat 504 as shown by probe 510a in FIG. 32, it can accurately monitor a number of conditions, and/or produce a number of measurements, for a large number of purposes, including the following: By monitoring body movements, the probe can alert the driver as to the onset of fatigue or drowsiness. By monitoring pulse and/or respiration, the probe can continuously inform the driver of the driver's health condition. By monitoring the weight or body distribution of the driver, the probe can make appropriate adjustments that may be desired with respect to actuating an airbag. In addition, by monitoring the driver's weight, body distribution, and possibly other parameters personal to the driver, the occupant of the driver's seat can be sufficiently identified and compared with corresponding personal data of person's authorized to operate the vehicle, to provide an indication of whether the seat is indeed occupied by an authorized person; and if not, to disable the operation of the vehicle, and/or to actuate an alarm.

Probe 510b applied to the rear seat 506 of the vehicle may be used for monitoring the same conditions of the rear seat occupants as described above and for the same purposes. In addition, the probe may be applied to a baby's seat to provide an indication of the "well-being" of the baby. For example, should cessation of breathing or lack of movement be detected, this condition may be automatically communicated to the driver of the vehicle by an alarm, light indicator, or the like.

Probe 510c for monitoring the space within the vehicle may be used as an anti-theft device to detect the presence of an unauthorized person within the vehicle, e.g., by the person's pulse, respiration, or movement, and to disable the vehicle and/or to sound an alarm.

While the probes illustrated in FIG. 32 are preferably of the type which measures the transit time between the transmitter and receiver of an energy pulse reflected from the deformable element, (e.g., membrane 10, FIG. 1), it will be appreciated that the probe could also be of the type which measures the transit time of an energy pulse through the membrane or other deformable element, since the length of such element is changed by its deformation, and this change in length is measurable by the probe, as also described above.

Figure 33:
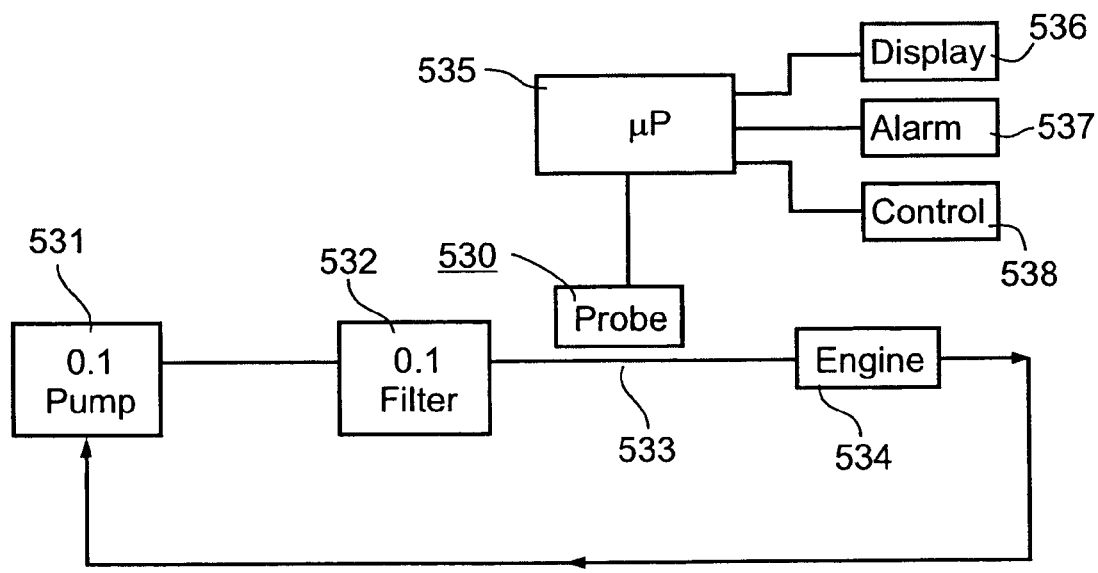
FIG. 33 diagrammatically illustrates an implementation for monitoring the composition of lubricating oil in a motor vehicle to produce an indication when the oil, and/or the oil filter, should be changed.

FIG. 33 illustrates another application of such a probe with respect to motor vehicles. In FIG. 33, the probe, generally designated 530, is used for monitoring the temperature and/or other condition of lubricating oil within the vehicle engine. Thus, as shown in FIG. 33, the lubricating oil is pumped from an oil pump 531 through an oil filter 532 via an oil line 533 to the vehicle engine 534. The probe 530 includes a transmitter and receiver, e.g., as described above with respect to FIG. 1, and is applied at any convenient location in the oil line 533. It is of sufficient sensitivity that its measuring circuit 534 can detect any changes in the temperature and/or composition of the oil which affect the transit time of the pulses transmitted between the transmitter and receiver within the probe, as described above. Thus, probe 530 can detect whether the oil within line 533 is relatively clean, or whether it includes undue quantities of dirt, debris, or other matter which might require changing the oil, and/or changing the oil filter. The condition of the oil can thus be continuously monitored and shown in a display 536, or used to actuate an alarm 537 should a change of oil or oil filter be indicated. The condition of the oil also provides an indication of the condition of the engine.

Probe 530 could be a hand probe manually applied at a convenient location in the oil line when such an oil check is to be made, or it could be permanently incorporated within the engine to continuously monitor the oil, oil filter, and/or engine condition. In either case, the transit time of the energy pulse, as measured by the measuring circuit 535, can be used to provide a display 536 of the oil, oil filter, and/or engine condition, and/or to actuate an alarm 537 to alert the driver that an oil change or other action is needed.

Such a probe could also include a displaceable heat-sensor as described above for immersion in the oil to measure its temperature. Another application of such a probe in motor vehicles would be to monitor the torque transmitted by the drive shaft, by sensing the deformation (strain) of the drive shaft.

Figure 34:
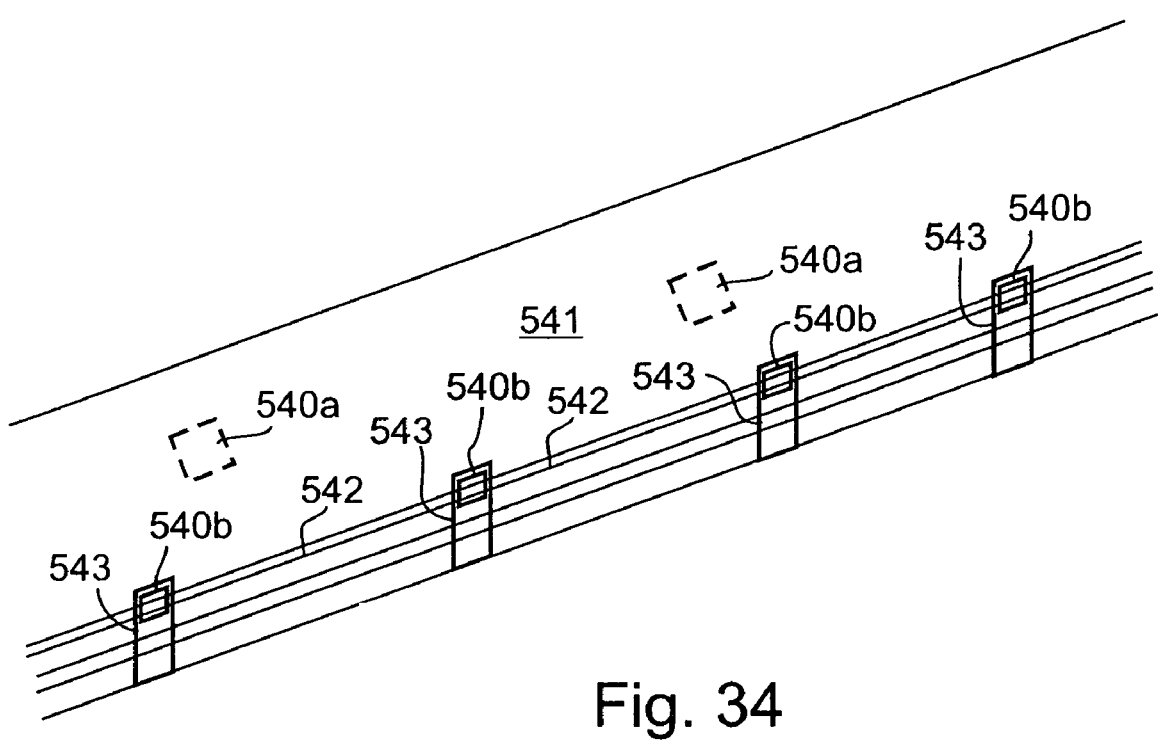
FIG. 34 diagrammatically illustrates an implementation for monitoring other secured spaces in order to detect intrusions therein.

FIG. 34 diagrammatically illustrates apparatus for monitoring other spaces, such as roads, spaces protected by fences or other barriers, etc., from intrusion by unauthorized persons. FIG. 34 illustrates a plurality of such probes, schematically indicated as 540a, for monitoring a road or path 541, and also a plurality of such probes, schematically indicated as 540b for monitoring a fence 542 or other barrier.

Probes 540a, 540b would be spaced along the length of the path 541 or fence 542 in order to detect intrusion by sensing movements, pulse, respiration, and/or other activity. For example, the road probes 540a could be buried under the road 541 or mounted to the side of the road; and the fence probes 540b could be mounted on the fence post 43. When the detection is based on detecting pulse or respiration, the system can easily distinguish between humans, animals, or other bodies that may have entered the protected space, in order to minimize false alarms.

While the invention has been described with respect to various preferred embodiments and illustrative applications, it will be appreciated that these are set forth merely for purposes of example. Many other embodiments and applications of the invention will be apparent to those skilled in the art, where the high precision and high resolution capabilities of the invention are required or can be utilized for detecting or measuring almost any condition or characteristic influencing the transit time of energy waves, both electromagnetic and sonic, from a transmitter to a receiver in a known or predeterminable manner.

What is claimed is:

1. A method of measuring a predetermined parameter, comprising:
   mounting a displaceable sensor on a mounting member such that the displaceable sensor changes its location, form or length with respect to said mounting member in accordance with said predetermined parameter;
   transmitting a cyclically-repeating energy wave through a transmission channel to or in said displaceable sensor;
   receiving said cyclically-repeating energy wave transmitted through said transmission channel to or in said displaceable sensor;
   continuously changing the frequency of transmission of the cyclically-repeating energy wave in accordance with changes in said predetermined parameter such that the number of waves received is a whole integer;

and utilizing the change in frequency to produce a measurement of said predetermined parameter.

2. The method according to claim 1, wherein said displaceable sensor is a deformable membrane.

3. The method according to claim 1, wherein said displaceable sensor is an end wall of a bellows.

4. The method according to claim 1, wherein said displaceable sensor is a spring-mounted member.

5. The method according to claim 1, wherein said displaceable sensor is a displaceable plunger.

6. The method according to claim 1, wherein said displaceable sensor is in the form of a bar or strip whose length and/or form changes in accordance with said predetermined parameter.

7. The method according to claim 1, wherein said displaceable sensor is constructed so as to be exposed for direct contact with a body such that the location or form of the sensor is changed by said body in accordance with the parameter to be measured, thereby changing the transit time of said cyclically-repeating energy waves transmitted to and reflected from said displaceable sensor in accordance with the parameter to be measured.

8. The method according to claim 1, wherein said displaceable sensor is constructed so as to be changed in location or form by a part of a person's body which pulsates according to the breathing rate and/or pulse rate of the person, said breathing rate and/or pulse rate being the parameter to be measured.

9. The method according to claim 1, wherein the displaceable sensor is constructed for direct contact with a body so as to be changed in length in accordance with the parameter to be measured, thereby changing the transit time of said cyclically-repeating energy waves transmitted through said displaceable sensor in accordance with the parameter to be measured.

10. The method according to claim 9, wherein said parameter to be measured is the temperature of said body.

11. The method according to claim 9, wherein said parameter to be measured is a mechanical force applied by said body against said displaceable sensor.

12. The method according to claim 1, wherein said transmitter and receiver are spaced apart a distance less than one wavelength of said energy pulses, and the triggering of the transmission of each energy pulse in the succession, by the reception of its preceding energy pulse, is delayed to add a "virtual distance" to the energy path.

13. Apparatus for measuring a predetermined parameter, comprising:

a displaceable sensor carried by a mounting member such that the displaceable sensor changes in location, form or length with respect to the mounting member in accordance with said predetermined parameter;

a transmitter for transmitting a cyclically-repeating energy wave through a transmission channel to or in said displaceable sensor;

a receiver for receiving said cyclically-repeating energy wave transmitted through said transmission channel to or in said displaceable sensor;

and a data processor for continuously changing the frequency of transmission of the cyclically-repeating energy wave in accordance with changes in said predetermined parameter such that the number of waves received is a whole integer and for utilizing the change in frequency to produce a measurement of said predetermined parameter.

14. The apparatus according to claim 13, wherein said displaceable sensor is a deformable membrane.

15. The apparatus according to claim 13, wherein said displaceable sensor is an end wall of a bellows.

16. The apparatus according to claim 13, wherein said displaceable sensor is a spring-mounted member.

17. The apparatus according to claim 13, wherein said displaceable sensor is a displaceable plunger.

18. The apparatus according to claim 13, wherein said displaceable sensor is in the form of a bar or strip whose length and/or form changes in accordance with said predetermined parameter.

19. The apparatus according to claim 13, wherein said displaceable sensor is constructed so as to be exposed for direct contact with a body such that the location or form of the sensor is changed by said body in accordance with the parameter to be measured, thereby changing the transit time of said cyclically-repeating energy waves transmitted to and reflected from said displaceable sensor in accordance with the parameter to be measured.

20. The apparatus according to claim 13, wherein said displaceable sensor is constructed to as to be changed in location or form by a part of a person's body which pulsates according to the breathing rate and/or pulse rate of the person, said breathing rate and/or pulse rate being the parameter to be measured.

21. The apparatus according to claim 13, wherein the displaceable sensor is constructed for direct contact with a body so as to be changed in length in accordance with the parameter to be measured, thereby changing the transit time of said cyclically-repeating energy waves transmitted through said displaceable sensor in accordance with the parameter to be measured.

22. The apparatus according to claim 21, wherein said displaceable sensor is constructed so as to change its length in accordance with the temperature of a body in contact therewith.

23. The apparatus according to claim 21, wherein said displaceable sensor is constructed so as to change its length in accordance with the mechanical force applied thereto by a body in contact therewith.

24. The apparatus according to claim 13, wherein said transmitter and receiver are spaced apart a distance less than one wavelength of said energy pulses, and the triggering of the transmission of each energy pulse in the succession, by the reception of its preceding energy pulse, is delayed to add a "virtual distance" to the energy path.

25. The apparatus according to claim 13, wherein said displaceable sensor is constructed so as to be changed in location, form or length by a part of a person's body according to a particular condition of the person to be measured.

26. The apparatus according to claim 25, wherein said displaceable sensor is incorporated in a mattress or seat to be occupied by the person, and said particular condition of the person to be measured is any movement of the person, the respiratory rate of the person, and/or the pulse rate of the person.

27. The apparatus according to claim 25, wherein said displaceable sensor is incorporated in a harness for application to the body of a person for measuring the respiratory rate of the person.

28. The apparatus according to claim 25, wherein said displaceable sensor is incorporated in a cuff for application to a limb of the person for measuring a cardiovascular condition of the person.

29. The apparatus according to claim 25, wherein said displaceable sensor is incorporated in a finger probe to be engaged by a finger of the person for measuring a cardiovascular condition of the person.

30. The apparatus according to claim 29, wherein said finger probe is incorporated in a cellular headset or other portable communication device.

31. The apparatus according to claim 25, wherein said displaceable sensor is incorporated in a pedometer for measuring the distance traversed by the person by foot.

32. The apparatus according to claim 25, wherein said displaceable sensor is incorporated in a probe including a handle for manipulating the probe to engage said displaceable sensor with a selected body part in accordance with the parameter to be measured.

33. The apparatus according to claim 32, wherein said displaceable sensor changes its length in accordance with the temperature of a body part engaged thereby.

34. The apparatus according to claim 25, wherein said displaceable sensor is constructed so as to be deployable via a catheter for measuring a predetermined parameter at a selected location of the person's body.

35. The apparatus according to claim 25, wherein said displaceable sensor is incorporated within a wound dressing to be applied over a wound in a person's body in order to measure one or more predetermined parameters providing an indication of the healing progress of the wound.

36. The apparatus according to claim 35, wherein said apparatus further includes a transponder which, upon being interrogated, transmits measurements of said one or more parameters in a wireless manner to an external receiver.

37. The apparatus according to claim 13, wherein said displaceable sensor is incorporated within a probe to be introduced into a heated chamber for measuring the temperature of the chamber.

38. The apparatus according to claim 13, wherein said displaceable sensor is incorporated within a vehicle seat for measuring a physical characteristic of an occupant of the seat.

39. The apparatus according to claim 13, wherein said displaceable sensor is incorporated within a secured area for sensing intrusions within said secured area.

40. The apparatus according to claim 13, wherein said displaceable sensor is incorporated within a probe constructed for immersion in a body of lubricating oil of an automotive vehicle for measuring the temperature of said lubricating oil.

41. The apparatus according to claim 40, wherein said probe also includes a sensor for providing an indication of the composition, and thereby of the cleanliness, of said lubricating oil.

42. Apparatus for monitoring the condition of lubricating oil in an automotive vehicle, comprising:

a transmitter at a first location with respect to a body of said lubricating oil for transmitting a cyclically-repeating energy wave through said body of lubricating oil;

a receiver at a second location with respect to said body of lubricating oil for receiving said cyclically-repeating energy waves after traversing said body of lubricating oil;

and a data processor for continuously changing the frequency of transmission of the cyclically-repeating energy wave in accordance with changes in said condition of the lubricating oil such that the number of waves received is a whole integer; and utilizing the change in frequency to produce an indication of the composition, and thereby of the cleanliness, of said lubricating oil.

43. The apparatus according to claim 42, wherein said apparatus further includes a displaceable sensor constructed for immersion in said body of lubricating oil for measuring the temperature thereof by measuring the change in length of said displaceable sensor.

* * * * *